US006610827B1

(12) United States Patent
Forsayeth et al.

(10) Patent No.: US 6,610,827 B1
(45) Date of Patent: Aug. 26, 2003

(54) POTASSIUM CHANNEL SUBUNIT POLYPEPTIDE AND POLYNUCLEOTIDE COMPOSITIONS AND USES THEREFOR

(75) Inventors: John R. Forsayeth, San Francisco, CA (US); Byron Zhao, Menlo Park, CA (US); Raymond A. Chavez, Alameda, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/181,339

(22) Filed: Oct. 28, 1998

Related U.S. Application Data

(60) Provisional application No. 60/063,450, filed on Oct. 29, 1997.

(51) Int. Cl.[7] .................................................. C07K 1/00
(52) U.S. Cl. ....................................................... 530/350
(58) Field of Search .......................................... 530/350

(56) References Cited

PUBLICATIONS

Genbank Direct Submission: Accession No. 2695871 $K^+$ channel protein.
Genbank Direct Submission: Accession No. 2815899 Shab–related delayed–rectifier $K^+$ channel alpha subunit.
Genbank Direct Submission: Accession No. 2815901 Delayed–rectifier $K^+$ channel alpha subunit.
Patel, A.J., et al., "Kv2.1/Kv9.3, a novel ATP–dependent delayed–rectifier $K^+$ channel in oxygen–sensitive pulmonary artery myocytes," The EMBO Journal 16(22): 6615–6625 (1997).

Post, M.A., et al,. "Kv2.1 and electrically silent Kv6.1 potassium channel subunits combine and express a novel current," FEBS Letters 399: 177–182 (1996).

Salinas, M. et al., "New Modulatory α Subunits for Mammalian Shab $K^+$ Channels," J. Biol Chem 272(39): 24371–24379 (1997).

Salinas, M., et al., "Modes of Regulation of Shab $K^+$ Channel Activity by the Kv8.1 Subunit," J. of Biol. Chem 272(13): 8774–8780 (1997).

Stocker, M., and Kerschensteiner, D., "Cloning and Tissue Distribution of Two New Potassium Channel α–Subunits from Rat Brain," Biochem Biophys Res Commun 248(3): 927–34 (1998).

Wang, J. et al., "Action of fenfluramine on voltage–gated $K^+$ channels in human pulmonary–artery smooth muscle cells," The Lancet 352: 290 (1998).

Weir, E.K., et al., "Anorexic Agents Aminorex, Fenfluramine, and Dexfenfluramine Inhibit Potassium Current in Rat Pulmonary Vascular Smooth Muscle and Cause Pulmonary Vasoconstriction," Circulation 94: 2216–2220 (1996).

*Primary Examiner*—Michael Pak
(74) *Attorney, Agent, or Firm*—Joanne R. Petithory; LeeAnn Gorthey; Perkins Coie LLP

(57) ABSTRACT

The present invention provides novel potassium channel subunits (denoted Kv-SL1 and Kv-SL2, and collectively as Kv-SL) and polynucleotides which identify and encode them. The invention also provides expression vectors and host cells comprising nucleic acid sequence encoding Kv-SL. The invention also provides antibodies of Kv-SL and methods of diagnosing and treating diseases associated with expression of Kv-SL, and screening assays employing the protein, nucleotide, and antibody compositions.

10 Claims, 24 Drawing Sheets

```
GGATCAGAAG AGCCACCGTG GACATTTGGC TTCCCAAATC CAAGCTTGTC CAGGAAAAAG    60
AGAGATGTCC CATACAAATC CCTAGTAGAT GCCAGGCCAT CCCACCATCC CATCACTCCA   120

ATAGCCCTGC AAGGGAGGCA CACTGTCGTA GCC ATG GTG AGC GAG TTT CCG GGT    174
                                     Met Val Ser Glu Phe Pro Gly
                                      1               5

CCA GGC TCT CGG GTC CCC TGG CGG CCT AGA GAC GAR GCG CTG CGC GTG     222
Pro Gly Ser Arg Val Pro Trp Arg Pro Arg Asp Xaa Ala Leu Arg Val
        10                  15                  20

AAC GTG GGC GGA GTG CGG CGG CTG CTG AGC GCG CGC GCC CTT GCG CGC     270
Asn Val Gly Gly Val Arg Arg Leu Leu Ser Ala Arg Ala Leu Ala Arg
    25                  30                  35

TTC CCG GGC ACG CGC CTG GGC CGC CTA CAG GCG GCG GCG TCC GAG GAG     318
Phe Pro Gly Thr Arg Leu Gly Arg Leu Gln Ala Ala Ala Ser Glu Glu
40                  45                  50                  55

CAG GCG CGG CGC CTG TGC GAC GAC TAC GAC GCA GCG GCG CAC GAG TTC     366
Gln Ala Arg Arg Leu Cys Asp Asp Tyr Asp Ala Ala Ala His Glu Phe
            60                  65                  70

TAC TTT GAT CGG CAT CCG GGC TTC TTT CTC GGC GTC CTA CAC TTC TAC     414
Tyr Phe Asp Arg His Pro Gly Phe Phe Leu Gly Val Leu His Phe Tyr
            75                  80                  85
```

Fig. 1A

```
CGC ACC GGG CAC CTG CAC GTC CTA GAC GAG CTG TGC GTC TTC GCC TTC      462
Arg Thr Gly His Leu His Val Leu Asp Glu Leu Cys Val Phe Ala Phe
         90                  95                 100

GGC CAG GAG GCT GAC TAC TGG GGC CTG GGC GAG AAC GCG CTG GCC ACG      510
Gly Gln Glu Ala Asp Tyr Trp Gly Leu Gly Glu Asn Ala Leu Ala Thr
    105                 110                 115

TGC TGC CGC GCG CGG TAT CTG GAG CGG CGT GTG GCG CGG CCT CGC GCC      558
Cys Cys Arg Ala Arg Tyr Leu Glu Arg Arg Val Ala Arg Pro Arg Ala
120                 125                 130                 135

TGG GAC GAG GAC AGC GAC GCG CCG AGC AGC GTG GAC CCG TGT CCC GAC      606
Trp Asp Glu Asp Ser Asp Ala Pro Ser Ser Val Asp Pro Cys Pro Asp
                140                 145                 150

GAG ATC TCG GAC GTG CAG CGG GAG CTG GCG CGC TAT GGT GCG GCT CGC      654
Glu Ile Ser Asp Val Gln Arg Glu Leu Ala Arg Tyr Gly Ala Ala Arg
            155                 160                 165

TGT GGC CGC CTG CGC CGT CGT CTC TGG CTC ACC ATG GAG AAT CCA GGC      702
Cys Gly Arg Leu Arg Arg Arg Leu Trp Leu Thr Met Glu Asn Pro Gly
        170                 175                 180

TAC TCG CTG CCC AGC AAG CTC TTC AGC TGC GTA TCC ATC GGC GTG GTG      750
Tyr Ser Leu Pro Ser Lys Leu Phe Ser Cys Val Ser Ile Gly Val Val
    185                 190                 195
```

Fig. 1B

```
CTC GCC TCC ATC GCT GCC ATG TGC ATC CAC AGC CTG CCG GAG TAC CAA      798
Leu Ala Ser Ile Ala Ala Met Cys Ile His Ser Leu Pro Glu Tyr Gln
200                 205                 210                 215

GCT CGG GAG GCG GCG GCG GCG GTG GCT GCA GTG GCC GCG GGT CGC AGC      846
Ala Arg Glu Ala Ala Ala Ala Val Ala Ala Val Ala Ala Gly Arg Ser
                220                 225                 230

GCA GAG GAG GTG CGC GAC GAC CCG GTG CTG CGC CGC CTG GAG TAC TTC      894
Ala Glu Glu Val Arg Asp Asp Pro Val Leu Arg Arg Leu Glu Tyr Phe
            235                 240                 245

TGC ATC GCT TGG TTC AGC TTC GAG GTG TCG TCG CGC CTG CTG CTG GCT      942
Cys Ile Ala Trp Phe Ser Phe Glu Val Ser Ser Arg Leu Leu Leu Ala
        250                 255                 260

CCC AGC ACG CGC AAC TTC TTC TGC CAC CCG CTC AAC CTC ATT GAC ATC      990
Pro Ser Thr Arg Asn Phe Phe Cys His Pro Leu Asn Leu Ile Asp Ile
    265                 270                 275

GTG TCG GTG CTG CCC TTC TAT CTC ACA CTG CTG GCT GGC GCA GCG CTT     1038
Val Ser Val Leu Pro Phe Tyr Leu Thr Leu Leu Ala Gly Ala Ala Leu
280                 285                 290                 295

GGT GAC CAG CGC GGA GCC AGC GGG GAG GAG CTC GGG GAC CTG GGC AAG     1086
Gly Asp Gln Arg Gly Ala Ser Gly Glu Glu Leu Gly Asp Leu Gly Lys
                300                 305                 310
```

Fig. 1C

```
GTA GTG CAA GTG TTC CGC CTC ATG CGC ATC TTC CGC GTG CTC AAG CTG     1134
Val Val Gln Val Phe Arg Leu Met Arg Ile Phe Arg Val Leu Lys Leu
            315                 320                 325

GCG CGC CAC TCC ACG GGG CTG CGT TCG CTG GGC GCC ACG CTC AAG CAC     1182
Ala Arg His Ser Thr Gly Leu Arg Ser Leu Gly Ala Thr Leu Lys His
        330                 335                 340

AGC TAC CGT GAG GTG GGC ATC TTA CTG CTG TAC CTG GCC GTG GGT GTG     1230
Ser Tyr Arg Glu Val Gly Ile Leu Leu Leu Tyr Leu Ala Val Gly Val
    345                 350                 355

TCA GTG TTC TCC GGC GTG GCC TAC ACA GCC GAA GAA GAA AAC GAG GGC     1278
Ser Val Phe Ser Gly Val Ala Tyr Thr Ala Glu Glu Glu Asn Glu Gly
360                 365                 370                 375

TTT CAC ACA ATC CCT GCC TGC TGG TGG TGG GGC ACA GTG AGC ATG ACC     1326
Phe His Thr Ile Pro Ala Cys Trp Trp Trp Gly Thr Val Ser Met Thr
                380                 385                 390

ACA GTG GGC TAT GGG GAT GTG GTG CCA GAG ACT GTG GGT GGC AAG CTG     1374
Thr Val Gly Tyr Gly Asp Val Val Pro Glu Thr Val Gly Gly Lys Leu
            395                 400                 405

GCG GCC TCG GGC TGC ATC CTC GGG GGC ATC CTG GTG GTC GCC CTC CCC     1422
Ala Ala Ser Gly Cys Ile Leu Gly Gly Ile Leu Val Val Ala Leu Pro
        410                 415                 420
```

Fig. 1D

```
ATC ACC ATC ATC TTC AAC AAG TTT TCC CAC TTC TAC CGG CGC CAG AAG    1470
Ile Thr Ile Ile Phe Asn Lys Phe Ser His Phe Tyr Arg Arg Gln Lys
    425                 430                 435

GCA CTG GAG GCG GCC GTG CGG AGC AGC GGT CAG CGC GAG TTT GAG GAC    1518
Ala Leu Glu Ala Ala Val Arg Ser Ser Gly Gln Arg Glu Phe Glu Asp
440                 445                 450                 455

TTG CTG AGT AGC GTT GAC GGG GTA TCG GAT GTG TCT CTG GAA ACA TCC    1566
Leu Leu Ser Ser Val Asp Gly Val Ser Asp Val Ser Leu Glu Thr Ser
                460                 465                 470

CGG GAC ACT TCT CAG GAG GGA CGC TTT ACA GAC CTG GAG ACC CAA GCT    1614
Arg Asp Thr Ser Gln Glu Gly Arg Phe Thr Asp Leu Glu Thr Gln Ala
            475                 480                 485

CCC CGG GAG CCT GCA AAA TCT CAC AGT TAT TAAAACCAGGGCTC TGTGTTCCCT   1668
Pro Arg Glu Pro Ala Lys Ser His Ser Tyr
        490                 495

CCCCACAGCC TGGGAATCAG CTAACACAGA GCAGAGTCCT CCCCTGCTTG GGGTCTGCAT   1728
GGGCGCCATC CACCTGAGCC GTCAGACATA GGGGCCACAG ATCTTTCTTG AAAAGCTCAG   1788
GCAGGATAGC ACAGCCCTAC ATTCTATGAG CACCGAGAGG AGGAAGAGGG CGGCCTCCAT   1848
AGGAGCCTTT TTAGCCTGGC AGATGATTAT CCCCATTTCA CAGATGAGGG CACTGAGGCC   1908
CAGCTGAATG CCACAGAGAA ATCACTAAGC CTTTGTCACT AAGTCCCTGG AAGGAGCTGG   1968
GGGGGGGGGG GGCTGGGTTT TTGGAATCTG TAGGATCCAT AGCACAATCA TCTACCACAC   2028
ACCTACTTCC TAGGGATGAC TTACAGAGAA AGCCTGAATA GACCCTTCTG GGACCCARAC   2088
```

Fig. 1E

```
CCAGCTCTAG ACCTGCCACA GGAAAGGTGG CCAAGGCCTG TCCCCARAAC TAGAGTCTAG    2148
CCAATCCGTC ACAGCATGTG ACCCAGAGAG GAGGTTACTG AGAAGGCCCA GCTCATCTCT    2208
GAACTGTTGG TGGCAGAGGG GTGCAGTTGC ATGCACCTGA CCTGACACAA GCTAAAGTTA    2268
CCTGGGAGGA GGAGCCTCCA CTGAGGGGAC ATCTCCATCA GATTGCTTGC AGGCAAGCCC    2328
GGTGAGACAT TAGCTTGATT AATGATTCAA TATGGGAGGG CCCAGCCCAC TGTGGGCAGT    2388
ACCACTCCCT CTCGGGTATA TAAGAAAGTA GACTGAACTG GCCACGGGAG CGAGTCAGTA    2448
AGCAGTGTTC CTCCATGGCC TCTGCTTCAG TTCCTGCTTG CAGGCTCCTG CCTTATGCTC    2508
CTGCCTTGGC ATCCCTCAGT GAACTATGAC CTGGGATATG TAAGCCAAAT AAACCCTTTC    2568
CTCTCCAAAA AAAAAAAAAA AAAAAAAAAA AAGGGCGGCC GCTCTARAGG ATCCCTCGAG    2628
GGGCCCAAGC TTACGCGTGC ATGCGACGTC ATAGCTCTCT CCCTATAGTG AGTCGTATTA    2688
TAAGCTAGGC ACTGGCCGTC GTTTTACAAC GTCGTGACTG GGAATCTGCT AGCTTGGGAT    2748
CTTTGTGAAG GAACCTTACT TCTGTGGTGT GACATAATTG GACAAACTAC               2798
```

Fig. 1F

```
C GTG GCT GCG GTG GCC GCG GGC CGC AGC CCG GAA GGC GTG CGC GAC GAC      49
  Val Ala Ala Val Ala Ala Gly Arg Ser Pro Glu Gly Val Arg Asp Asp
   1               5                  10                  15

CCG GTG CTG CGA CGC CTC GAG TAC TTC TGC ATC GCC TGG TTC AGC TTC        97
Pro Val Leu Arg Arg Leu Glu Tyr Phe Cys Ile Ala Trp Phe Ser Phe
            20                  25                  30

GAG GTG TCG TCG CGC CTC CTG CTG GCG CCC AGT ACG CGC AAC TTC TTC       145
Glu Val Ser Ser Arg Leu Leu Leu Ala Pro Ser Thr Arg Asn Phe Phe
        35                  40                  45

TGC CAC CCG CTC AAC CTC ATC GAC ATT GTG TCT GTG CTG CCC TTC TAT       193
Cys His Pro Leu Asn Leu Ile Asp Ile Val Ser Val Leu Pro Phe Tyr
    50                  55                  60

CTC ACG CTG CTG GCT GGT GTG GCA CTG GGC GAC CAG GGC GGC AAG GAG       241
Leu Thr Leu Leu Ala Gly Val Ala Leu Gly Asp Gln Gly Gly Lys Glu
65                  70                  75                  80

TTC GGC CAC CTG GGC AAG GTG GTG CAG GTG TTC CGC CTC ATG CGC ATC       289
Phe Gly His Leu Gly Lys Val Val Gln Val Phe Arg Leu Met Arg Ile
                85                  90                  95

TTC CGC GTA CTC AAG TTG GCG CGC CAT TCC ACC GGG CTG CGC TCG CTG       337
Phe Arg Val Leu Lys Leu Ala Arg His Ser Thr Gly Leu Arg Ser Leu
            100                 105                 110
```

Fig. 2A

```
GGA GCC ACG CTC AAG CAC AGC TAC CGT GAR GTG GGC ATC TTG CTG CTG      385
Gly Ala Thr Leu Lys His Ser Tyr Arg Xaa Val Gly Ile Leu Leu Leu
        115                 120                 125

TAC CTG GCT GTG GGT GTG TCA GTG TTC TCT GGT GTG GCC TAC ACA GCT      433
Tyr Leu Ala Val Gly Val Ser Val Phe Ser Gly Val Ala Tyr Thr Ala
    130                 135                 140

GAA AAG GAG GAG GAC GTG GGC TTT AAC ACC ATC CCA GCC TGC TGG TGG      481
Glu Lys Glu Glu Asp Val Gly Phe Asn Thr Ile Pro Ala Cys Trp Trp
145                 150                 155                 160

TGG GGC ACA GTG AGC ATG ACC ACC GTG GGC TAT GGG GAT GTG GTG CCA      529
Trp Gly Thr Val Ser Met Thr Thr Val Gly Tyr Gly Asp Val Val Pro
                165                 170                 175

GTG ACG GTG GCT GGC AAG CTG GCA GCC TCA GGC TGC ATC CTA GGG GGC      577
Val Thr Val Ala Gly Lys Leu Ala Ala Ser Gly Cys Ile Leu Gly Gly
            180                 185                 190

ATC CTG GTG GTA GCA CTC CCC ATC ACC ATC ATC TTC AAC AAG TTC TCC      625
Ile Leu Val Val Ala Leu Pro Ile Thr Ile Ile Phe Asn Lys Phe Ser
        195                 200                 205

CAC TTC TAC CGG CGC CAG AAG GCT CTG GAG GCA GCC GTG CGC AAC AGC      673
His Phe Tyr Arg Arg Gln Lys Ala Leu Glu Ala Ala Val Arg Asn Ser
    210                 215                 220
```

Fig. 2B

```
AAC CAC CAA GAG TTT GAG GAC TTG CTG AGC AGC ATT GAT GGG GTG TCG      721
Asn His Gln Glu Phe Glu Asp Leu Leu Ser Ser Ile Asp Gly Val Ser
225                 230                 235                 240

GAG GCA TCT CTG GAG ACA TCC CGA GAA ACC TCT CAG GAG GGA CAG TCT      769
Glu Ala Ser Leu Glu Thr Ser Arg Glu Thr Ser Gln Glu Gly Gln Ser
                245                 250                 255

GCA GA                                                                774
Ala
```

Fig. 2C

```
GCCTGCAGGT ACCGGTCCGG AAWTTCCCGG GTYGACCCAC GCGTCCGGCG GACTCGGCGA    60
CCCGTGCGGG CTAGCCCGCT CTCCTGCCGC TGCGGCGGCG GGCGCGGGGC TGCGCGGCGA   120
GGCCGGATCC CTGCAGCACG GACAGGCGGC GTCGCAGAAC CCAGCCAGCC AGACGCGCCA   180
AGACTCCCGA CTCCTGCAGG TGAACTTGAC TTTACAGCAA CTGCTTTGAC TTGGACAACC   240
GGAGGGCCAC ATTCTTCTCT TCTTTGAGCA CTAAATGCCG GTGCACACTC CACCCTCCAG   300
CAAGGGAAGA CAGGAGGAGC TTCTTGGATG ACAATGGAGG TTCCACTGTG CAGGATGAGG   360
GCAGGCTGTA TGACATCGCC ACCACGARGG TTCAGCGTGA TCTCCTGTGT CTCCCTTCCA   420

GGCCAGCACT CTGCCTTCTC AATCCATC ATG GTG TTT GGT GAG TTT TTC CAT      472
                               Met Val Phe Gly Glu Phe Phe His
                                1               5

CGC CCT GGA CAA GAT GAG GAA CTT GTC AAC TTG AAC GTG GGG GGC TTT      520
Arg Pro Gly Gln Asp Glu Glu Leu Val Asn Leu Asn Val Gly Gly Phe
    10                  15                  20

AAG CAG TCT GTG GAT CAA AGT ACA CTC CTG CGG TTC CCT CAC ACA CGA      568
Lys Gln Ser Val Asp Gln Ser Thr Leu Leu Arg Phe Pro His Thr Arg
25                  30                  35                  40

CTG GGA AAG CTG CTT ACC TGC CAC TCT GAG GAG GCC ATT CTG GAG CTG      616
Leu Gly Lys Leu Leu Thr Cys His Ser Glu Glu Ala Ile Leu Glu Leu
                45                  50                  55

TGT GAT GAC TAC AGC GTG GCA GAT AAA GAG TAC TAC TTT GAT CGG AAC      664
Cys Asp Asp Tyr Ser Val Ala Asp Lys Glu Tyr Tyr Phe Asp Arg Asn
            60                  65                  70
```

Fig. 3A

```
CCC TTC CTG TTC AGA TAC GTC TTG AAC TTT TAT TAC ACA GGG AAG CTG      712
Pro Phe Leu Phe Arg Tyr Val Leu Asn Phe Tyr Tyr Thr Gly Lys Leu
        75                  80                  85

CAT GTG ATG GAG GAA CTG TGT GTC TTC TCC TTC TGC CAG GAG ATC GAG      760
His Val Met Glu Glu Leu Cys Val Phe Ser Phe Cys Gln Glu Ile Glu
    90                  95                  100

TAC TGG GGC ATC AAT GAG CTC TTC ATT GAC TCC TGC TGT AGC AGT CGG      808
Tyr Trp Gly Ile Asn Glu Leu Phe Ile Asp Ser Cys Cys Ser Ser Arg
105                 110                 115                 120

TAC CAG GAG CGC AAG GAG GAG AGC CAC GAC AAG GAC TGG GAC CAG AAA      856
Tyr Gln Glu Arg Lys Glu Glu Ser His Asp Lys Asp Trp Asp Gln Lys
                125                 130                 135

AGC AAC GAT GTG AGC ACA GAC TCC TCC TTT GAA GAA TCG TCT CTG TTT      904
Ser Asn Asp Val Ser Thr Asp Ser Ser Phe Glu Glu Ser Ser Leu Phe
            140                 145                 150

GAG AAA GAG CTG GAG AAG TTT GAT GAG CTG AGA TTT GGT CAG CTC CGA      952
Glu Lys Glu Leu Glu Lys Phe Asp Glu Leu Arg Phe Gly Gln Leu Arg
        155                 160                 165

AAG AAG ATC TGG ATT CGA ATG GAA AAT CCA GCT TAC TGC CTG TCG GCC     1000
Lys Lys Ile Trp Ile Arg Met Glu Asn Pro Ala Tyr Cys Leu Ser Ala
    170                 175                 180
```

Fig. 3B

```
AAG CTC ATT GCC ATC TCC TCC TTG AGC GTG GTG CTG GCT TCC ATA GTG     1048
Lys Leu Ile Ala Ile Ser Ser Leu Ser Val Val Leu Ala Ser Ile Val
185                 190                 195                 200

GCC ATG TGT GTG CAC AGC ATG TCG GAA TTC CAG AAC GAG GAT GGA GAA     1096
Ala Met Cys Val His Ser Met Ser Glu Phe Gln Asn Glu Asp Gly Glu
                205                 210                 215

GTG GAT GAC CCT GTG CTG GAA GGT GTG GAG ATT GCC TGC ATT GCA TGG     1144
Val Asp Asp Pro Val Leu Glu Gly Val Glu Ile Ala Cys Ile Ala Trp
            220                 225                 230

TTT ACT GGT GAG CTA GCC ATC AGG CTG GTT GCT GCT CCA TCA CAA AAG     1192
Phe Thr Gly Glu Leu Ala Ile Arg Leu Val Ala Ala Pro Ser Gln Lys
        235                 240                 245

AAG TTC TGG AAA AAC CCT CTG AAC ATC ATT GAC TTT GTT TCT ATC ATT     1240
Lys Phe Trp Lys Asn Pro Leu Asn Ile Ile Asp Phe Val Ser Ile Ile
    250                 255                 260

CCC TTC TAT GCC ACG TTG GCT GTG GAC ACC AAG GAA GAA GAG AGT GAG     1288
Pro Phe Tyr Ala Thr Leu Ala Val Asp Thr Lys Glu Glu Glu Ser Glu
265                 270                 275                 280

GAC ATT GAG AAT ATG GGC AAG GTG GTC CAG ATC CTT CGG CTC ATG AGG     1336
Asp Ile Glu Asn Met Gly Lys Val Val Gln Ile Leu Arg Leu Met Arg
                285                 290                 295
```

Fig. 3C

```
ATT TTC CGA ATT CTG AAG CTT GCC CGG CAC TCT GTA GGG CTT CGG TCT     1384
Ile Phe Arg Ile Leu Lys Leu Ala Arg His Ser Val Gly Leu Arg Ser
            300                 305                 310

CTT GGG GCC ACA CTG AGG CAC AGT TAC CAT GAG GTG GGG CTA CTG CTT     1432
Leu Gly Ala Thr Leu Arg His Ser Tyr His Glu Val Gly Leu Leu Leu
        315                 320                 325

CTC TTC CTT TCT GTG GGC ATC TCC ATC TTC TCT GTG CTT ATC TAC TCT     1480
Leu Phe Leu Ser Val Gly Ile Ser Ile Phe Ser Val Leu Ile Tyr Ser
    330                 335                 340

GTG GAG AAA GAT GAA CAC AAG TCC AGT CTC ACC AGC ATC CCC ATC TGC     1528
Val Glu Lys Asp Glu His Lys Ser Ser Leu Thr Ser Ile Pro Ile Cys
345                 350                 355                 360

TGG TGG TGG GCC ACT ATC AGT ATG ACC ACA GTG GGC TAT GGA GAC ACC     1576
Trp Trp Trp Ala Thr Ile Ser Met Thr Thr Val Gly Tyr Gly Asp Thr
                365                 370                 375

CAC CCA GTC ACC TTA GCT GGG AAA ATC ATT GCA AGC ACA TGT ATT ATC     1624
His Pro Val Thr Leu Ala Gly Lys Ile Ile Ala Ser Thr Cys Ile Ile
            380                 385                 390

TGT GGA ATC TTA GTG GTA GCC CTC CCC ATT ACC ATC ATC TTC AAC AAG     1672
Cys Gly Ile Leu Val Val Ala Leu Pro Ile Thr Ile Ile Phe Asn Lys
        395                 400                 405
```

Fig. 3D

```
TTT TCC AAG TAC TAC CAG AAG CAG AAA GAC ATG GAA GTG GAC CAG TGC     1720
Phe Ser Lys Tyr Tyr Gln Lys Gln Lys Asp Met Glu Val Asp Gln Cys
    410                 415                 420

AGC GAG GAC CCA CCA GAG AAG TGC CAT GAG CTA CCG TAC TTT AAC ATT     1768
Ser Glu Asp Pro Pro Glu Lys Cys His Glu Leu Pro Tyr Phe Asn Ile
425                 430                 435                 440

AGG GAC GTT TAT GCA CAG CAA GTA CAT GCC TTC ATC ACC AGT CTG TCT     1816
Arg Asp Val Tyr Ala Gln Gln Val His Ala Phe Ile Thr Ser Leu Ser
                445                 450                 455

TCC ATT GGC ATC GTG GTC AGT GAT CCT GAC TCC ACA GAT GCT TCG AGC     1864
Ser Ile Gly Ile Val Val Ser Asp Pro Asp Ser Thr Asp Ala Ser Ser
            460                 465                 470

GTT GAA GAC AAT GAG GAT GCT TAC AAC ACT GCA TCC CTG GAG AAC TGT     1912
Val Glu Asp Asn Glu Asp Ala Tyr Asn Thr Ala Ser Leu Glu Asn Cys
        475                 480                 485

ACT GGA AAA TGAGCAGGGG CATTTGCACA GATATCTCGT GTCCCTTCCT GACATTAGG  1970
Thr Gly Lys
    490

TTAACACAGC TTTATAAACC TCAATGGGTT TGTTCAAAAA ATCATTTAAT TCTCAGGGTG   2030
TACCTTTTAG CCATAGTTGG ACATTCATTG CTGAATTCTG AAATGATAGA ATTATCTTTA   2090
TTTTTCTCAG TGAGATCAAT TAAAATGCCT TGTTCTGAAA TTTATTTTTT ACAAGAGAGA   2150
```

Fig. 3E

```
GTTGTAATAC GGTTTTTTGG GGAAAAAAGT AAATGATATT GGGAAGGATT TATTGCTACG    2210
GCTTACGCAT CATTCTATAT TTGCCATTCA CTCACATTGA GCTAACTATA AATTACTGAT    2270
GATAGAGCAG AGGCCCAGCT GACTGAAGAT GACGACATGC ATGTAAGATC TACAACATGA    2330
GACAATGCAT GTAAATCCAT GTTCATGTTC CAGACATGGG AATTAGGAGC CCAATAAACT    2390
TCTAATTTGG TATGGAGAAA AAAAAAAAAA AAAGGGCGGC CGCTCTAGAG GATCCCTCGA    2450
GGGGCCCAAG CTTACGCGTG CATGCRACGT CATACCCCTC CC                       2492
```

Fig. 3F

```
G TCG ACC TGG ATT AGA ATG GAG AAT CCA GCG TAC TGC CTG TCC GCT AAG     49
  Ser Thr Trp Ile Arg Met Glu Asn Pro Ala Tyr Cys Leu Ser Ala Lys
   1               5                  10                  15

CTT ATC GCT ATC TCC TCC TTG AGC GTG GTG CTG GCC TCC ATC GTG GCC       97
Leu Ile Ala Ile Ser Ser Leu Ser Val Val Leu Ala Ser Ile Val Ala
            20                  25                  30

ATG TGC GTT CAC AGC ATG TCG GAG TTC CAG AAT GAG GAT GGA GAA GTG      145
Met Cys Val His Ser Met Ser Glu Phe Gln Asn Glu Asp Gly Glu Val
        35                  40                  45

GAT GAT CCG GTG CTG GAA GGA GTG GAG ATC GCG TGC ATT GCC TGG TTC      193
Asp Asp Pro Val Leu Glu Gly Val Glu Ile Ala Cys Ile Ala Trp Phe
    50                  55                  60

ACC GGG GAG CTT GCC GTC CGG CTG GCT GCC GCT CCT TGT CAA AAG AAA      241
Thr Gly Glu Leu Ala Val Arg Leu Ala Ala Ala Pro Cys Gln Lys Lys
65                  70                  75                  80

TTC TGG AAA AAC CCT CTG AAC ATC ATT GAC TTT GTC TCT ATT ATT CCC      289
Phe Trp Lys Asn Pro Leu Asn Ile Ile Asp Phe Val Ser Ile Ile Pro
                85                  90                  95

TTC TAT GCC ACG TCG ACC TGG ATT AGA ATG GAG AAT CCA GCG TAC TGC      337
Phe Tyr Ala Thr Ser Thr Trp Ile Arg Met Glu Asn Pro Ala Tyr Cys
            100                 105                 110
```

Fig. 4A

```
CTG TCC GCT AAG CTT ATC GCT ATC TCC TCC TTG AGC GTG GTG CTG GCC    385
Leu Ser Ala Lys Leu Ile Ala Ile Ser Ser Leu Ser Val Val Leu Ala
        115                 120                 125

TCC ATC GTG GCC ATG TGC GTT CAC AGC ATG TCG GAG TTC CAG AAT GAG    433
Ser Ile Val Ala Met Cys Val His Ser Met Ser Glu Phe Gln Asn Glu
    130                 135                 140

GAT GGA GAA GTG GAT GAT CCG GTG CTG GAA GGA GTG GAG ATC GCG TGC    481
Asp Gly Glu Val Asp Asp Pro Val Leu Glu Gly Val Glu Ile Ala Cys
145                 150                 155                 160

ATT GCC TGG TTC ACC GGG GAG CTT GCC GTC CGG CTG GCT GCC GCT CCT    529
Ile Ala Trp Phe Thr Gly Glu Leu Ala Val Arg Leu Ala Ala Ala Pro
                165                 170                 175

TGT CAA AAG AAA TTC TGG AAA AAC CCT CTG AAC ATC ATT GAC TTT GTC    577
Cys Gln Lys Lys Phe Trp Lys Asn Pro Leu Asn Ile Ile Asp Phe Val
            180                 185                 190

TCT ATT ATT CCC TTC TAT GCC ACG TTG GGC TGT AGA CAC CAA GGA GGA    625
Ser Ile Ile Pro Phe Tyr Ala Thr Leu Gly Cys Arg His Gln Gly Gly
        195                 200                 205

AGA GAG GTG AGG ATA TTG AGA AAC ATG GGC AAG GTG GTC CAG ATC CTA    673
Arg Glu Val Arg Ile Leu Arg Asn Met Gly Lys Val Val Gln Ile Leu
    210                 215                 220
```

Fig. 4B

```
CGG CTT ATG AGG ATT TTC CGA ATT CTA AAG CTT GCC CGG CAC TCG GTA     721
Arg Leu Met Arg Ile Phe Arg Ile Leu Lys Leu Ala Arg His Ser Val
225                 230                 235                 240

GGA CTT CGG TCT CTA GGT GCC ACA CTG AGA CAC AGC TAC CAT GAA GTT     769
Gly Leu Arg Ser Leu Gly Ala Thr Leu Arg His Ser Tyr His Glu Val
                245                 250                 255

GGG TTT CTG CTT CTC TTC CTC TCT GTG GGC ATT TCC ATT TTC TCT GTG     817
Gly Phe Leu Leu Leu Phe Leu Ser Val Gly Ile Ser Ile Phe Ser Val
            260                 265                 270

CTT ATC TAC TCC GTG GAG AAA GAT GAC CAC ACA TCC AGC CTC ACC AGC     865
Leu Ile Tyr Ser Val Glu Lys Asp Asp His Thr Ser Ser Leu Thr Ser
        275                 280                 285

ATC CCC ATC TGC TGG TGG TGG GCC ACC ATC AGC ATG ACA ACT GTG GGC     913
Ile Pro Ile Cys Trp Trp Trp Ala Thr Ile Ser Met Thr Thr Val Gly
    290                 295                 300

TAT GGA GAC ACC CAC CCG GTC ACC TTG GCG GGA AAG CTC ATC GCC AGC     961
Tyr Gly Asp Thr His Pro Val Thr Leu Ala Gly Lys Leu Ile Ala Ser
305                 310                 315                 320

ACA TGC ATC ATC TGT GGC ATC TTG GTG GTG GCC CTT CCC ATC ACC ATC    1009
Thr Cys Ile Ile Cys Gly Ile Leu Val Val Ala Leu Pro Ile Thr Ile
                325                 330                 335
```

Fig. 4C

```
ATC TTC AAC AAG TTT TCC AAG TAC TAC CAG AAG CAA AAG GAC ATT GAT     1057
Ile Phe Asn Lys Phe Ser Lys Tyr Tyr Gln Lys Gln Lys Asp Ile Asp
            340                 345                 350

GTG GAC CAG TGC AGT GAG GAT GCA CCA GAG AAG TGT CAT GAG CTA CCT     1105
Val Asp Gln Cys Ser Glu Asp Ala Pro Glu Lys Cys His Glu Leu Pro
        355                 360                 365

TAC TTT AAC ATT AGG GAT ATA TAT GCA CAG CGG ATG CAC ACC TTC ATT     1153
Tyr Phe Asn Ile Arg Asp Ile Tyr Ala Gln Arg Met His Thr Phe Ile
    370                 375                 380

ACC AGT CTC TCT TCT GTA GGC ATT GTG GTG AGC GAT CCT GAC TCC ACA     1201
Thr Ser Leu Ser Ser Val Gly Ile Val Val Ser Asp Pro Asp Ser Thr
385                 390                 395                 400

GAT GCT TCA AGC ATT GAA GAC AAT GAG GAC ATT TGT AAC ACC ACC TCC     1249
Asp Ala Ser Ser Ile Glu Asp Asn Glu Asp Ile Cys Asn Thr Thr Ser
                405                 410                 415

TTG GAG AAT TGC ACA GCA AAA TGA                                      1273
Leu Glu Asn Cys Thr Ala Lys
            420
```

Fig. 4D

```
                                  10                                      20                                      30
SEQ ID 3   M V S E F P G P G S R V P W R P R D E A L R V N V G G V R R
SEQ ID 5
SEQ ID 7                   M V F G E F F H R P G Q D E E L V N L N V G G F K Q
SEQ ID 9

                                  40                                      50                                      60
SEQ ID 3   L L S A R A L A R F P G T R L G R L Q A A A S E E Q A R R L
SEQ ID 5
SEQ ID 7   S V D Q S T L L R F P H T R L G K L L T C H S E E A I L E L
SEQ ID 9

                                  70                                      80                                      90
SEQ ID 3   C D D Y D A A A H E F Y F D R H P G F F L G V L H F Y R T G
SEQ ID 5
SEQ ID 7   C D D Y S V A D K E Y Y F D R N P F L F R Y V L N F Y Y T G
SEQ ID 9

                                  100                                     110                                     120
SEQ ID 3   H L H V L D E L C V F A F G Q E A D Y W G L G E N A L A T C
SEQ ID 5
SEQ ID 7   K L H V M E E L C V F S F C Q E I E Y W G I N E L F I D S C
SEQ ID 9

                                  130                                     140                                     150
SEQ ID 3   C R A R Y L E R R V A R P R A W D E D S D A P S S V D P C P
SEQ ID 5
SEQ ID 7   C S S R Y Q E R K E E S H D K D W D Q K S N D V S T D S S F
SEQ ID 9

                                  160                                     170                                     180
SEQ ID 3   D E I S D V Q R E L A R Y G A A R C G R L R R R L W L T M E
SEQ ID 5
SEQ ID 7   E E S S L F E K E L E K F D E L R F G Q L R K K I W I R M E
SEQ ID 9                                                     S T W I R M E

                                  190                                     200                                     210
SEQ ID 3   N P G Y S L P S K L F S C V S I G V V L A S I A A M C I H S
SEQ ID 5
SEQ ID 7   N P A Y C L S A K L I A I S S L S V V L A S I V A M C V H S
SEQ ID 9   N P A Y C L S A K L I A I S S L S V V L A S I V A M C V H S

                                  220                                     230                                     240
SEQ ID 3   L P E Y Q A R E A A A A V A A V A A G R S A E E V R D D P V
SEQ ID 5                           V A A V A A G R S P E G V R D D P V
SEQ ID 7   M S E F Q - - - - - - - - - - - - - - - N E D G E V D D P V
SEQ ID 9   M S E F Q - - - - - - - - - - - - - - - N E D G E V D D P V
```

Fig. 5A

```
            250                 260                 270
SEQ ID 3  L R R L E Y F C I A W F S F E V S S R L L L A P S T R N F F
SEQ ID 5  L R R L E Y F C I A W F S F E V S S R L L L A P S T R N F F
SEQ ID 7  L E G V E I A C I A W F T G E L A I R L V A A P S Q K K F W
SEQ ID 9  L E G V E I A C I A W F T G E L A V R L A A A P C Q K K F W

            280                 290                 300
SEQ ID 3  C H P L N L I D I V S V L P F Y L T L L A G A A L G D Q R G
SEQ ID 5  C H P L N L I D I V S V L P F Y L T L L A G V A L G D Q - -
SEQ ID 7  K N P L N I I D F V S I I P F Y A T L A V D T K E - E E - -
SEQ ID 9  K N P L N I I D F V S I I P F Y A T L G C R H Q G G R E - -

            310                 320                 330
SEQ ID 3  A S G E E L G D L G K V V Q V F R L M R I F R V L K L A R H
SEQ ID 5  - G G K E F G H L G K V V Q V F R L M R I F R V L K L A R H
SEQ ID 7  - - S E D I E N M G K V V Q I L R L M R I F R I L K L A R H
SEQ ID 9  - - V R I L R N M G K V V Q I L R L M R I F R I L K L A R H

            340                 350                 360
SEQ ID 3  S T G L R S L G A T L K H S Y R E V G I L L L Y L A V G V S
SEQ ID 5  S T G L R S L G A T L K H S Y R E V G I L L L Y L A V G V S
SEQ ID 7  S V G L R S L G A T L R H S Y H E V G L L L L F L S V G I S
SEQ ID 9  S V G L R S L G A T L R H S Y H E V G F L L L F L S V G I S

            370                 380                 390
SEQ ID 3  V F S G V A Y T A E - - E E N E G F H T I P A C W W W G T V
SEQ ID 5  V F S G V A Y T A E K - E E D V G F N T I P A C W W W G T V
SEQ ID 7  I F S V L I Y S V E K D E H K S S L T S I P I C W W W A T I
SEQ ID 9  I F S V L I Y S V E K D D H T S S L T S I P I C W W W A T I

            400                 410                 420
SEQ ID 3  S M T T V G Y G D V V P E T V G G K L A A S G C I L G G I L
SEQ ID 5  S M T T V G Y G D V V P V T V A G K L A A S G C I L G G I L
SEQ ID 7  S M T T V G Y G D T H P V T L A G K I I A S T C I I C G I L
SEQ ID 9  S M T T V G Y G D T H P V T L A G K L I A S T C I I C G I L

            430                 440                 450
SEQ ID 3  V V A L P I T I I F N K F S H F Y R R Q K A L E A A V R S S
SEQ ID 5  V V A L P I T I I F N K F S H F Y R R Q K A L E A A V R N S
SEQ ID 7  V V A L P I T I I F N K F S K Y Y Q K Q K D M E V D Q C S E
SEQ ID 9  V V A L P I T I I F N K F S K Y Y Q K Q K D I D V D Q C S E

            460                 470                 480
SEQ ID 3  G Q R E - - - - - - - - - - - - - - F E D L L S S V D G V S
SEQ ID 5  N H Q E - - - - - - - - - - - - - - F E D L L S S I D G V S
SEQ ID 7  D P P E K C H E L P Y F N I R D V Y A Q Q V H A F I T S L S
SEQ ID 9  D A P E K C H E L P Y F N I R D I Y A Q R M H T F I T S L S
```

Fig. 5B

```
                                 490                  500                  510
SEQ ID 3   D V S L E T S R D T S Q E G R F T D L E T Q A P R E P A K S
SEQ ID 5   E A S L E T S R E T S Q E G Q S A
SEQ ID 7   S I G I V V S D P D S T D A S S V E D N E D A Y N T A S L E
SEQ ID 9   S V G I V V S D P D S T D A S S I E D N E D I C N T T S L E

                                 520                  530                  540
SEQ ID 3   H S Y
SEQ ID 5
SEQ ID 7   N C T G K
SEQ ID 9   N C T A K
```

Fig. 5C

```
SEQID 3     1 MVSEFPGPGSRVPWRPRDEALRVNVGGVRRLLSARALARFPGTRLGRLQA  50
SEQID 5                                                          0

SEQID 3    51 AASEEQARRLCDDYDAAAHEFYFDRHPGFFLGVLHFYRTGHLHVLDELCV 100
SEQID 5                                                          0

SEQID 3   101 FAFGQEADYWGLGENALATCCRARYLERRVARPRAWDEDSDAPSSVDPCP 150
SEQID 5                                                          0

SEQID 3   151 DEISDVQRELARYGAARCGRLRRRLWLTMENPGYSLPSKLFSCVSIGVVL 200
SEQID 5                                                          0

SEQID 3   201 ASIAAMCIHSLPEYQAREAAAAVAAVAAGRSAEEVRDDPVLRRLEYFCIA 250
SEQID 5     1                       VAAVAAGRSPEGVRDDPVLRRLEYFCIA  28
                                    ********* * ***************

SEQID 3   251 WFSFEVSSRLLLAPSTRNFFCHPLNLIDIVSVLPFYLTLLAGAALGDQRG 300
SEQID 5    29 WFSFEVSSRLLLAPSTRNFFCHPLNLIDIVSVLPFYLTLLAGVALGDQ--  76
              ****************************************** *****

SEQID 3   301 ASGEELGDLGKVVQVFRLMRIFRVLKLARHSTGLRSLGATLKHSYREVGI 350
SEQID 5    77 -GGKEFGHLGKVVQVFRLMRIFRVLKLARHSTGLRSLGATLKHSYREVGI 125
                * * * ******************************************

SEQID 3   351 LLLYLAVGVSVFSGVAYTAE-EENEGFHTIPACWWWGTVSMTTVGYGDVV 399
SEQID 5   126 LLLYLAVGVSVFSGVAYTAEKEEDVGFNTIPACWWWGTVSMTTVGYGDVV 175
              ******************** **  ** *********************

SEQID 3   400 PETVGGKLAASGCILGGILVVALPITIIFNKFSHFYRRQKALEAAVRSSG 449
SEQID 5   176 PVTVAGKLAASGCILGGILVVALPITIIFNKFSHFYRRQKALEAAVRNSN 225
              * ** *************************************** *

SEQID 3   450 QREFEDLLSSVDGVSDVSLETSRDTSQEGRFTDLETQAPREPAKSHSY 497
SEQID 5   226 HQEFEDLLSSIDGVSEASLETSRETSQEGQSA                 257
                ******** ****  ****** *****
```

Fig. 6

```
SEQID 7     1 MVFGEFFHRPGQDEELVNLNVGGFKQSVDQSTLLRFPHTRLGKLLTCHSE  50
SEQID 9                                                         0

SEQID 7    51 EAILELCDDYSVADKEYYFDRNPFLFRYVLNFYYTGKLHVMEELCVFSFC 100
SEQID 9                                                         0

SEQID 7   101 QEIEYWGINELFIDSCCSSRYQERKEESHDKDWDQKSNDVSTDSSFEESS 150
SEQID 9                                                         0

SEQID 7   151 LFEKELEKFDELRFGQLRKKIWIRMENPAYCLSAKLIAISSLSVVLASIV 200
SEQID 9     1                    STWIRMENPAYCLSAKLIAISSLSVVLASIV  31
                                   ****************************

SEQID 7   201 AMCVHSMSEFQNEDGEVDDPVLEGVEIACIAWFTGELAIRLVAAPSQKKF 250
SEQID 9    32 AMCVHSMSEFQNEDGEVDDPVLEGVEIACIAWFTGELAVRLAAAPCQKKF  81
              ************************************** ** *** ****

SEQID 7   251 WKNPLNIIDFVSIIPFYATLAVDTKE-EESEDIENMGKVVQILRLMRIFR 299
SEQID 9    82 WKNPLNIIDFVSIIPFYATLGCRHQGGREVRILRNMGKVVQILRLMRIFR 131
              ********************        *     ***************

SEQID 7   300 ILKLARHSVGLRSLGATLRHSYHEVGLLLLFLSVGISIFSVLIYSVEKDE 349
SEQID 9   132 ILKLARHSVGLRSLGATLRHSYHEVGFLLLFLSVGISIFSVLIYSVEKDD 181
              ************************** ***********************

SEQID 7   350 HKSSLTSIPICWWWATISMTTVGYGDTHPVTLAGKIIASTCIICGILVVA 399
SEQID 9   182 HTSSLTSIPICWWWATISMTTVGYGDTHPVTLAGKLIASTCIICGILVVA 231
              * ********************************* **************

SEQID 7   400 LPITIIFNKFSKYYQKQKDMEVDQCSEDPPEKCHELPYFNIRDVYAQQVH 449
SEQID 9   232 LPITIIFNKFSKYYQKQKDIDVDQCSEDAPEKCHELPYFNIRDIYAQRMH 281
              *******************  ******* ************** ***  *

SEQID 7   450 AFITSLSSIGIVVSDPDSTDASSVEDNEDAYNTASLENCTGK 491
SEQID 9   282 TFITSLSSVGIVVSDPDSTDASSIEDNEDICNTTSLENCTAK 323
               ******* ************** *****  ** ****** *
```

Fig. 7

SEQUENCE LISTING

```
<160> NUMBER OF SEQ ID NOS: 12

<210> SEQ ID NO 1
<211> LENGTH: 625
<212> TYPE: DNA
<213> ORGANISM: Homo sapiens

<400> SEQUENCE: 1

cgtggctgcg gtggccgcgg gccgcagccc ggaaggcgtg cgcgacgacc cggtgctgcg     60

acgcctcgag tacttctgca tcgcctggtt cagcttcgag gtgtcgtcgc gcctcctgct    120
```

-continued

```
ggcgcccagt acgcgcaact tcttctgcca cccgctcaac ctcatcgaca ttgtgtctgt    180

gctgcccttc tatctcacgc tgctggctgg tgtggcactg ggcgaccagg gcggcaagga    240

gttcggccac ctgggcaagg tggtgcaggt gttccgcctc atgcgcatct tccgcgtact    300

caagttggcg cgccattcca ccgggctgcg ctcgctggga gccacgctca agcacagcta    360

ccgtgargtg ggcatcttgc tgctgtacct ggctgtgggt gtgtcagtgt tctctggtgt    420

ggcctacaca gctgaaaagg aggaggacgt gggctttaac accatcccag cctgctggtg    480

gtggggcaca gtgagcatga ccaccgtggg ctatggggat gtggtgccag tgacggtggc    540

tggcaagctg gcagcctcag gctgcatcct agggggcatc ctggtggtag cactccccat    600

caccatcatc ttcaacaagt tctcc                                          625


<210> SEQ ID NO 2
<211> LENGTH: 2799
<212> TYPE: DNA
<213> ORGANISM: Mus musculus
<220> FEATURE:
<221> NAME/KEY: CDS
<222> LOCATION: (154)...(1647)
<221> NAME/KEY: misc_feature
<222> LOCATION: (1)...(2799)
<223> OTHER INFORMATION: n = A,T,C or G

<400> SEQUENCE: 2

ggatcagaag agccaccgtg gacatttggc ttcccaaatc caagcttgtc caggaaaaag     60

agagatgtcc catacaaatc cctagtagat gccaggccat cccaccatcc catcactcca    120

atagccctgc aagggaggca cactgtcgta gcc atg gtg agc gag ttt ccg ggt     174
                                     Met Val Ser Glu Phe Pro Gly
                                      1               5

cca ggc tct cgg gtc ccc tgg cgg cct aga gac gar gcg ctg cgc gtg      222
Pro Gly Ser Arg Val Pro Trp Arg Pro Arg Asp Glu Ala Leu Arg Val
         10                  15                  20

aac gtg ggc gga gtg cgg cgg ctg ctg agc gcg cgc gcc ctt gcg cgc      270
Asn Val Gly Gly Val Arg Arg Leu Leu Ser Ala Arg Ala Leu Ala Arg
     25                  30                  35

ttc ccg ggc acg cgc ctg ggc cgc cta cag gcg gcg gcg tcc gag gag      318
Phe Pro Gly Thr Arg Leu Gly Arg Leu Gln Ala Ala Ala Ser Glu Glu
 40                  45                  50                  55

cag gcg cgg cgc ctg tgc gac gac tac gac gca gcg gcg cac gag ttc      366
Gln Ala Arg Arg Leu Cys Asp Asp Tyr Asp Ala Ala Ala His Glu Phe
                 60                  65                  70

tac ttt gat cgg cat ccg ggc ttc ttt ctc ggc gtc cta cac ttc tac      414
Tyr Phe Asp Arg His Pro Gly Phe Phe Leu Gly Val Leu His Phe Tyr
             75                  80                  85

cgc acc ggg cac ctg cac gtc cta gac gag ctg tgc gtc ttc gcc ttc      462
Arg Thr Gly His Leu His Val Leu Asp Glu Leu Cys Val Phe Ala Phe
         90                  95                 100

ggc cag gag gct gac tac tgg ggc ctg ggc gag aac gcg ctg gcc acg      510
Gly Gln Glu Ala Asp Tyr Trp Gly Leu Gly Glu Asn Ala Leu Ala Thr
    105                 110                 115

tgc tgc cgc gcg cgg tat ctg gag cgg cgt gtg gcg cgg cct cgc gcc      558
Cys Cys Arg Ala Arg Tyr Leu Glu Arg Arg Val Ala Arg Pro Arg Ala
120                 125                 130                 135

tgg gac gag gac agc gac gcg ccg agc agc gtg gac ccg tgt ccc gac      606
Trp Asp Glu Asp Ser Asp Ala Pro Ser Ser Val Asp Pro Cys Pro Asp
                140                 145                 150

gag atc tcg gac gtg cag cgg gag ctg gcg cgc tat ggt gcg gct cgc      654
Glu Ile Ser Asp Val Gln Arg Glu Leu Ala Arg Tyr Gly Ala Ala Arg
```

-continued

```
            155                 160                 165

tgt ggc cgc ctg cgc cgt cgt ctc tgg ctc acc atg gag aat cca ggc      702
Cys Gly Arg Leu Arg Arg Arg Leu Trp Leu Thr Met Glu Asn Pro Gly
        170                 175                 180

tac tcg ctg ccc agc aag ctc ttc agc tgc gta tcc atc ggc gtg gtg      750
Tyr Ser Leu Pro Ser Lys Leu Phe Ser Cys Val Ser Ile Gly Val Val
    185                 190                 195

ctc gcc tcc atc gct gcc atg tgc atc cac agc ctg ccg gag tac caa      798
Leu Ala Ser Ile Ala Ala Met Cys Ile His Ser Leu Pro Glu Tyr Gln
200                 205                 210                 215

gct cgg gag gcg gcg gcg gcg gtg gct gca gtg gcc gcg ggt cgc agc      846
Ala Arg Glu Ala Ala Ala Ala Val Ala Ala Val Ala Ala Gly Arg Ser
            220                 225                 230

gca gag gag gtg cgc gac gac ccg gtg ctg cgc cgc ctg gag tac ttc      894
Ala Glu Glu Val Arg Asp Asp Pro Val Leu Arg Arg Leu Glu Tyr Phe
            235                 240                 245

tgc atc gct tgg ttc agc ttc gag gtg tcg tcg cgc ctg ctg ctg gct      942
Cys Ile Ala Trp Phe Ser Phe Glu Val Ser Ser Arg Leu Leu Leu Ala
        250                 255                 260

ccc agc acg cgc aac ttc ttc tgc cac ccg ctc aac ctc att gac atc      990
Pro Ser Thr Arg Asn Phe Phe Cys His Pro Leu Asn Leu Ile Asp Ile
    265                 270                 275

gtg tcg gtg ctg ccc ttc tat ctc aca ctg ctg gct ggc gca gcg ctt     1038
Val Ser Val Leu Pro Phe Tyr Leu Thr Leu Leu Ala Gly Ala Ala Leu
280                 285                 290                 295

ggt gac cag cgc gga gcc agc ggg gag gag ctc ggg gac ctg ggc aag     1086
Gly Asp Gln Arg Gly Ala Ser Gly Glu Glu Leu Gly Asp Leu Gly Lys
            300                 305                 310

gta gtg caa gtg ttc cgc ctc atg cgc atc ttc cgc gtg ctc aag ctg     1134
Val Val Gln Val Phe Arg Leu Met Arg Ile Phe Arg Val Leu Lys Leu
            315                 320                 325

gcg cgc cac tcc acg ggg ctg cgt tcg ctg ggc gcc acg ctc aag cac     1182
Ala Arg His Ser Thr Gly Leu Arg Ser Leu Gly Ala Thr Leu Lys His
        330                 335                 340

agc tac cgt gag gtg ggc atc tta ctg ctg tac ctg gcc gtg ggt gtg     1230
Ser Tyr Arg Glu Val Gly Ile Leu Leu Leu Tyr Leu Ala Val Gly Val
    345                 350                 355

tca gtg ttc tcc ggc gtg gcc tac aca gcc gaa gaa gaa aac gag ggc     1278
Ser Val Phe Ser Gly Val Ala Tyr Thr Ala Glu Glu Glu Asn Glu Gly
360                 365                 370                 375

ttt cac aca atc cct gcc tgc tgg tgg tgg ggc aca gtg agc atg acc     1326
Phe His Thr Ile Pro Ala Cys Trp Trp Trp Gly Thr Val Ser Met Thr
            380                 385                 390

aca gtg ggc tat ggg gat gtg gtg cca gag act gtg ggt ggc aag ctg     1374
Thr Val Gly Tyr Gly Asp Val Val Pro Glu Thr Val Gly Gly Lys Leu
            395                 400                 405

gcg gcc tcg ggc tgc atc ctc ggg ggc atc ctg gtg gtc gcc ctc ccc     1422
Ala Ala Ser Gly Cys Ile Leu Gly Gly Ile Leu Val Val Ala Leu Pro
        410                 415                 420

atc acc atc atc ttc aac aag ttt tcc cac ttc tac cgg cgc cag aag     1470
Ile Thr Ile Ile Phe Asn Lys Phe Ser His Phe Tyr Arg Arg Gln Lys
    425                 430                 435

gca ctg gag gcg gcc gtg cgg agc agc ggt cag cgc gag ttt gag gac     1518
Ala Leu Glu Ala Ala Val Arg Ser Ser Gly Gln Arg Glu Phe Glu Asp
440                 445                 450                 455

ttg ctg agt agc gtt gac ggg gta tcg gat gtg tct ctg gaa aca tcc     1566
Leu Leu Ser Ser Val Asp Gly Val Ser Asp Val Ser Leu Glu Thr Ser
            460                 465                 470

cgg gac act tct cag gag gga cgc ttt aca gac ctg gag acc caa gct     1614
```

-continued

```
Arg Asp Thr Ser Gln Glu Gly Arg Phe Thr Asp Leu Glu Thr Gln Ala
            475                 480                 485

ccc cgg gag cct gca aaa tct cac agt tat taa aaccagggct ctgtgttccc   1667
Pro Arg Glu Pro Ala Lys Ser His Ser Tyr
        490                 495

tccccacagc ctgggaatca gctaacacag agcagagtcc tcccctgctt ggggtctgca   1727

tgggcgccat ccacctgagc cgtcagacat aggggccaca gatctttctt gaaaagctca   1787

ggcaggatag cacagcccta cattctatga gcaccgagag gaggaagagg gcggcctcca   1847

taggagcctt tttagcctgg cagatgatta tccccatttc acagatgagg gcactgaggc   1907

ccagctgaat gccacagaga aatcactaag cctttgtcac taagtccctg gaaggagctg   1967

gggggggggg gggctgggtt tttggaatct gtaggatcca tagcacaatc atctaccaca   2027

cacctacttc ctagggatga cttacagaga aagcctgaat agacccttct gggacccara   2087

cccagctcta gacctgccac aggaaaggtg gccaaggcct gtccccaraa ctagagtcta   2147

gccaatccgt cacagcatgt gacccagaga ggaggttact gagaaggccc agctcatctc   2207

tgaactgttg gtggcagagg ggtgcagttg catgcacctg acctgacaca agctaaagtt   2267

acctgggagg aggagcctcc actgagggga catctccatc agattgcttg caggcaagcc   2327

cggtgagaca ttagcttgat taatgattca atatgggagg gcccagccca ctgtgggcag   2387

taccactccc tctcgggtat ataagaaagt agactgaact ggccacggga gcgagtcagt   2447

aagcagtgtt cctccatggc ctctgcttca gttcctgctt gcaggctcct gccttatgct   2507

cctgccttgg catccctcag tgaactatga cctgggatat gtaagccaaa taaacccttt   2567

cctctccaaa aaaaaaaaaa aaaaaaaaaa aaagggcggc cgctctarag gatccctcga   2627

ggggcccaag cttacgcgtg catgcgacgt catagctctc tccctatagt gagtcgtatt   2687

ataagctagg cactggccgt cgttttacaa cgtcgtgact ggganatctg ctagcttggg   2747

atctttgtga aggaacctta cttctgtggt gtgacataat tggacaaact ac           2799


<210> SEQ ID NO 3
<211> LENGTH: 497
<212> TYPE: PRT
<213> ORGANISM: Mus musculus

<400> SEQUENCE: 3

Met Val Ser Glu Phe Pro Gly Pro Gly Ser Arg Val Pro Trp Arg Pro
 1               5                  10                  15

Arg Asp Glu Ala Leu Arg Val Asn Val Gly Gly Val Arg Arg Leu Leu
            20                  25                  30

Ser Ala Arg Ala Leu Ala Arg Phe Pro Gly Thr Arg Leu Gly Arg Leu
        35                  40                  45

Gln Ala Ala Ala Ser Glu Glu Gln Ala Arg Arg Leu Cys Asp Asp Tyr
    50                  55                  60

Asp Ala Ala Ala His Glu Phe Tyr Phe Asp Arg His Pro Gly Phe Phe
65                  70                  75                  80

Leu Gly Val Leu His Phe Tyr Arg Thr Gly His Leu His Val Leu Asp
                85                  90                  95

Glu Leu Cys Val Phe Ala Phe Gly Gln Glu Ala Asp Tyr Trp Gly Leu
            100                 105                 110

Gly Glu Asn Ala Leu Ala Thr Cys Cys Arg Ala Arg Tyr Leu Glu Arg
        115                 120                 125

Arg Val Ala Arg Pro Arg Ala Trp Asp Glu Asp Ser Asp Ala Pro Ser
    130                 135                 140
```

-continued

```
Ser Val Asp Pro Cys Pro Asp Glu Ile Ser Asp Val Gln Arg Glu Leu
145                 150                 155                 160

Ala Arg Tyr Gly Ala Ala Arg Cys Gly Arg Leu Arg Arg Arg Leu Trp
                165                 170                 175

Leu Thr Met Glu Asn Pro Gly Tyr Ser Leu Pro Ser Lys Leu Phe Ser
            180                 185                 190

Cys Val Ser Ile Gly Val Val Leu Ala Ser Ile Ala Ala Met Cys Ile
        195                 200                 205

His Ser Leu Pro Glu Tyr Gln Ala Arg Glu Ala Ala Ala Ala Val Ala
    210                 215                 220

Ala Val Ala Ala Gly Arg Ser Ala Glu Glu Val Arg Asp Asp Pro Val
225                 230                 235                 240

Leu Arg Arg Leu Glu Tyr Phe Cys Ile Ala Trp Phe Ser Phe Glu Val
                245                 250                 255

Ser Ser Arg Leu Leu Leu Ala Pro Ser Thr Arg Asn Phe Phe Cys His
            260                 265                 270

Pro Leu Asn Leu Ile Asp Ile Val Ser Val Leu Pro Phe Tyr Leu Thr
        275                 280                 285

Leu Leu Ala Gly Ala Ala Leu Gly Asp Gln Arg Gly Ala Ser Gly Glu
    290                 295                 300

Glu Leu Gly Asp Leu Gly Lys Val Val Gln Val Phe Arg Leu Met Arg
305                 310                 315                 320

Ile Phe Arg Val Leu Lys Leu Ala Arg His Ser Thr Gly Leu Arg Ser
                325                 330                 335

Leu Gly Ala Thr Leu Lys His Ser Tyr Arg Glu Val Gly Ile Leu Leu
            340                 345                 350

Leu Tyr Leu Ala Val Gly Val Ser Val Phe Ser Gly Val Ala Tyr Thr
        355                 360                 365

Ala Glu Glu Glu Asn Glu Gly Phe His Thr Ile Pro Ala Cys Trp Trp
    370                 375                 380

Trp Gly Thr Val Ser Met Thr Thr Val Gly Tyr Gly Asp Val Val Pro
385                 390                 395                 400

Glu Thr Val Gly Gly Lys Leu Ala Ala Ser Gly Cys Ile Leu Gly Gly
                405                 410                 415

Ile Leu Val Val Ala Leu Pro Ile Thr Ile Ile Phe Asn Lys Phe Ser
            420                 425                 430

His Phe Tyr Arg Arg Gln Lys Ala Leu Glu Ala Ala Val Arg Ser Ser
        435                 440                 445

Gly Gln Arg Glu Phe Glu Asp Leu Leu Ser Ser Val Asp Gly Val Ser
    450                 455                 460

Asp Val Ser Leu Glu Thr Ser Arg Asp Thr Ser Gln Glu Gly Arg Phe
465                 470                 475                 480

Thr Asp Leu Glu Thr Gln Ala Pro Arg Glu Pro Ala Lys Ser His Ser
                485                 490                 495

Tyr


<210> SEQ ID NO 4
<211> LENGTH: 774
<212> TYPE: DNA
<213> ORGANISM: Homo sapiens
<220> FEATURE:
<221> NAME/KEY: CDS
<222> LOCATION: (2)...(772)

<400> SEQUENCE: 4
```

-continued

```
c gtg gct gcg gtg gcc gcg ggc cgc agc ccg gaa ggc gtg cgc gac gac      49
  Val Ala Ala Val Ala Ala Gly Arg Ser Pro Glu Gly Val Arg Asp Asp
   1               5                  10                  15

ccg gtg ctg cga cgc ctc gag tac ttc tgc atc gcc tgg ttc agc ttc        97
Pro Val Leu Arg Arg Leu Glu Tyr Phe Cys Ile Ala Trp Phe Ser Phe
            20                  25                  30

gag gtg tcg tcg cgc ctc ctg ctg gcg ccc agt acg cgc aac ttc ttc       145
Glu Val Ser Ser Arg Leu Leu Leu Ala Pro Ser Thr Arg Asn Phe Phe
        35                  40                  45

tgc cac ccg ctc aac ctc atc gac att gtg tct gtg ctg ccc ttc tat       193
Cys His Pro Leu Asn Leu Ile Asp Ile Val Ser Val Leu Pro Phe Tyr
    50                  55                  60

ctc acg ctg ctg gct ggt gtg gca ctg ggc gac cag ggc ggc aag gag       241
Leu Thr Leu Leu Ala Gly Val Ala Leu Gly Asp Gln Gly Gly Lys Glu
65                  70                  75                  80

ttc ggc cac ctg ggc aag gtg gtg cag gtg ttc cgc ctc atg cgc atc       289
Phe Gly His Leu Gly Lys Val Val Gln Val Phe Arg Leu Met Arg Ile
                85                  90                  95

ttc cgc gta ctc aag ttg gcg cgc cat tcc acc ggg ctg cgc tcg ctg       337
Phe Arg Val Leu Lys Leu Ala Arg His Ser Thr Gly Leu Arg Ser Leu
            100                 105                 110

gga gcc acg ctc aag cac agc tac cgt gar gtg ggc atc ttg ctg ctg       385
Gly Ala Thr Leu Lys His Ser Tyr Arg Glu Val Gly Ile Leu Leu Leu
        115                 120                 125

tac ctg gct gtg ggt gtg tca gtg ttc tct ggt gtg gcc tac aca gct       433
Tyr Leu Ala Val Gly Val Ser Val Phe Ser Gly Val Ala Tyr Thr Ala
    130                 135                 140

gaa aag gag gag gac gtg ggc ttt aac acc atc cca gcc tgc tgg tgg       481
Glu Lys Glu Glu Asp Val Gly Phe Asn Thr Ile Pro Ala Cys Trp Trp
145                 150                 155                 160

tgg ggc aca gtg agc atg acc acc gtg ggc tat ggg gat gtg gtg cca       529
Trp Gly Thr Val Ser Met Thr Thr Val Gly Tyr Gly Asp Val Val Pro
                165                 170                 175

gtg acg gtg gct ggc aag ctg gca gcc tca ggc tgc atc cta ggg ggc       577
Val Thr Val Ala Gly Lys Leu Ala Ala Ser Gly Cys Ile Leu Gly Gly
            180                 185                 190

atc ctg gtg gta gca ctc ccc atc acc atc atc ttc aac aag ttc tcc       625
Ile Leu Val Val Ala Leu Pro Ile Thr Ile Ile Phe Asn Lys Phe Ser
        195                 200                 205

cac ttc tac cgg cgc cag aag gct ctg gag gca gcc gtg cgc aac agc       673
His Phe Tyr Arg Arg Gln Lys Ala Leu Glu Ala Ala Val Arg Asn Ser
    210                 215                 220

aac cac caa gag ttt gag gac ttg ctg agc agc att gat ggg gtg tcg       721
Asn His Gln Glu Phe Glu Asp Leu Leu Ser Ser Ile Asp Gly Val Ser
225                 230                 235                 240

gag gca tct ctg gag aca tcc cga gaa acc tct cag gag gga cag tct       769
Glu Ala Ser Leu Glu Thr Ser Arg Glu Thr Ser Gln Glu Gly Gln Ser
                245                 250                 255

gca ga                                                                774


<210> SEQ ID NO 5
<211> LENGTH: 256
<212> TYPE: PRT
<213> ORGANISM: Homo sapiens

<400> SEQUENCE: 5

Val Ala Ala Val Ala Ala Gly Arg Ser Pro Glu Gly Val Arg Asp Asp
 1               5                  10                  15

Pro Val Leu Arg Arg Leu Glu Tyr Phe Cys Ile Ala Trp Phe Ser Phe
```

-continued

```
            20                  25                  30

Glu Val Ser Ser Arg Leu Leu Leu Ala Pro Ser Thr Arg Asn Phe Phe
        35                  40                  45

Cys His Pro Leu Asn Leu Ile Asp Ile Val Ser Val Leu Pro Phe Tyr
    50                  55                  60

Leu Thr Leu Leu Ala Gly Val Ala Leu Gly Asp Gln Gly Gly Lys Glu
65                  70                  75                  80

Phe Gly His Leu Gly Lys Val Val Gln Val Phe Arg Leu Met Arg Ile
                85                  90                  95

Phe Arg Val Leu Lys Leu Ala Arg His Ser Thr Gly Leu Arg Ser Leu
            100                 105                 110

Gly Ala Thr Leu Lys His Ser Tyr Arg Glu Val Gly Ile Leu Leu Leu
        115                 120                 125

Tyr Leu Ala Val Gly Val Ser Val Phe Ser Gly Val Ala Tyr Thr Ala
    130                 135                 140

Glu Lys Glu Glu Asp Val Gly Phe Asn Thr Ile Pro Ala Cys Trp Trp
145                 150                 155                 160

Trp Gly Thr Val Ser Met Thr Thr Val Gly Tyr Gly Asp Val Val Pro
                165                 170                 175

Val Thr Val Ala Gly Lys Leu Ala Ala Ser Gly Cys Ile Leu Gly Gly
            180                 185                 190

Ile Leu Val Val Ala Leu Pro Ile Thr Ile Ile Phe Asn Lys Phe Ser
        195                 200                 205

His Phe Tyr Arg Arg Gln Lys Ala Leu Glu Ala Ala Val Arg Asn Ser
    210                 215                 220

Asn His Gln Glu Phe Glu Asp Leu Leu Ser Ser Ile Asp Gly Val Ser
225                 230                 235                 240

Glu Ala Ser Leu Glu Thr Ser Arg Glu Thr Ser Gln Glu Gly Gln Ser
                245                 250                 255


<210> SEQ ID NO 6
<211> LENGTH: 2494
<212> TYPE: DNA
<213> ORGANISM: Mus musculus
<220> FEATURE:
<221> NAME/KEY: CDS
<222> LOCATION: (449)...(1924)
<221> NAME/KEY: misc_feature
<222> LOCATION: (1)...(2494)
<223> OTHER INFORMATION: n = A,T,C or G

<400> SEQUENCE: 6

gcctgcaggt accggtccgg aawttcccgg gtygacccac gcgtccggcg gactcggcga      60

cccgtgcggg ctagcccgct ctcctgccgc tgcggcggcg ggcgcggggc tgcgcggcga     120

ggccggatcc ctgcagcacg gacaggcggc gtcgcagaac ccagccagcc agacgcgcca     180

agactcccga ctcctgcagg tgaacttgac tttacagcaa ctgctttgac ttggacaacc     240

ggagggccac attcttctct tctttgagca ctaaatgccg gtgcacactc caccctccag     300

caagggaaga caggaggagc ttcttggatg acaatggagg ttccactgtg caggatgagg     360

gcaggctgta tgacatcgcc accacgargg ttcagcgtga tctcctgtgt ctcccttcca     420

ggccagcact ctgccttctc aatccatc atg gtg ttt ggt gag ttt ttc cat        472
                               Met Val Phe Gly Glu Phe Phe His
                                1               5

cgc cct gga caa gat gag gaa ctt gtc aac ttg aac gtg ggg ggc ttt       520
Arg Pro Gly Gln Asp Glu Glu Leu Val Asn Leu Asn Val Gly Gly Phe
     10                  15                  20
```

-continued

```
aag cag tct gtg gat caa agt aca ctc ctg cgg ttc cct cac aca cga      568
Lys Gln Ser Val Asp Gln Ser Thr Leu Leu Arg Phe Pro His Thr Arg
 25                  30                  35                  40

ctg gga aag ctg ctt acc tgc cac tct gag gag gcc att ctg gag ctg      616
Leu Gly Lys Leu Leu Thr Cys His Ser Glu Glu Ala Ile Leu Glu Leu
                 45                  50                  55

tgt gat gac tac agc gtg gca gat aaa gag tac tac ttt gat cgg aac      664
Cys Asp Asp Tyr Ser Val Ala Asp Lys Glu Tyr Tyr Phe Asp Arg Asn
             60                  65                  70

ccc ttc ctg ttc aga tac gtc ttg aac ttt tat tac aca ggg aag ctg      712
Pro Phe Leu Phe Arg Tyr Val Leu Asn Phe Tyr Tyr Thr Gly Lys Leu
         75                  80                  85

cat gtg atg gag gaa ctg tgt gtc ttc tcc ttc tgc cag gag atc gag      760
His Val Met Glu Glu Leu Cys Val Phe Ser Phe Cys Gln Glu Ile Glu
     90                  95                 100

tac tgg ggc atc aat gag ctc ttc att gac tcc tgc tgt agc agt cgg      808
Tyr Trp Gly Ile Asn Glu Leu Phe Ile Asp Ser Cys Cys Ser Ser Arg
105                 110                 115                 120

tac cag gag cgc aag gag gag agc cac gac aag gac tgg gac cag aaa      856
Tyr Gln Glu Arg Lys Glu Glu Ser His Asp Lys Asp Trp Asp Gln Lys
                125                 130                 135

agc aac gat gtg agc aca gac tcc tcc ttt gaa gaa tcg tct ctg ttt      904
Ser Asn Asp Val Ser Thr Asp Ser Ser Phe Glu Glu Ser Ser Leu Phe
            140                 145                 150

gag aaa gag ctg gag aag ttt gat gag ctg aga ttt ggt cag ctc cga      952
Glu Lys Glu Leu Glu Lys Phe Asp Glu Leu Arg Phe Gly Gln Leu Arg
        155                 160                 165

aag aag atc tgg att cga atg gaa aat cca gct tac tgc ctg tcg gcc     1000
Lys Lys Ile Trp Ile Arg Met Glu Asn Pro Ala Tyr Cys Leu Ser Ala
    170                 175                 180

aag ctc att gcc atc tcc tcc ttg agc gtg gtg ctg gct tcc ata gtg     1048
Lys Leu Ile Ala Ile Ser Ser Leu Ser Val Val Leu Ala Ser Ile Val
185                 190                 195                 200

gcc atg tgt gtg cac agc atg tcg gaa ttc cag aac gag gat gga gaa     1096
Ala Met Cys Val His Ser Met Ser Glu Phe Gln Asn Glu Asp Gly Glu
                205                 210                 215

gtg gat gac cct gtg ctg gaa ggt gtg gag att gcc tgc att gca tgg     1144
Val Asp Asp Pro Val Leu Glu Gly Val Glu Ile Ala Cys Ile Ala Trp
            220                 225                 230

ttt act ggt gag cta gcc atc agg ctg gtt gct gct cca tca caa aag     1192
Phe Thr Gly Glu Leu Ala Ile Arg Leu Val Ala Ala Pro Ser Gln Lys
        235                 240                 245

aag ttc tgg aaa aac cct ctg aac atc att gac ttt gtt tct atc att     1240
Lys Phe Trp Lys Asn Pro Leu Asn Ile Ile Asp Phe Val Ser Ile Ile
    250                 255                 260

ccc ttc tat gcc acg ttg gct gtg gac acc aag gaa gaa gag agt gag     1288
Pro Phe Tyr Ala Thr Leu Ala Val Asp Thr Lys Glu Glu Glu Ser Glu
265                 270                 275                 280

gac att gag aat atg ggc aag gtg gtc cag atc ctt cgg ctc atg agg     1336
Asp Ile Glu Asn Met Gly Lys Val Val Gln Ile Leu Arg Leu Met Arg
                285                 290                 295

att ttc cga att ctg aag ctt gcc cgg cac tct gta ggg ctt cgg tct     1384
Ile Phe Arg Ile Leu Lys Leu Ala Arg His Ser Val Gly Leu Arg Ser
            300                 305                 310

ctt ggg gcc aca ctg agg cac agt tac cat gag gtg ggg cta ctg ctt     1432
Leu Gly Ala Thr Leu Arg His Ser Tyr His Glu Val Gly Leu Leu Leu
        315                 320                 325

ctc ttc ctt tct gtg ggc atc tcc atc ttc tct gtg ctt atc tac tct     1480
Leu Phe Leu Ser Val Gly Ile Ser Ile Phe Ser Val Leu Ile Tyr Ser
```

-continued

```
    330                 335                 340

gtg gag aaa gat gaa cac aag tcc agt ctc acc agc atc ccc atc tgc      1528
Val Glu Lys Asp Glu His Lys Ser Ser Leu Thr Ser Ile Pro Ile Cys
345                 350                 355                 360

tgg tgg tgg gcc act atc agt atg acc aca gtg ggc tat gga gac acc      1576
Trp Trp Trp Ala Thr Ile Ser Met Thr Thr Val Gly Tyr Gly Asp Thr
                365                 370                 375

cac cca gtc acc tta gct ggg aaa atc att gca agc aca tgt att atc      1624
His Pro Val Thr Leu Ala Gly Lys Ile Ile Ala Ser Thr Cys Ile Ile
            380                 385                 390

tgt gga atc tta gtg gta gcc ctc ccc att acc atc atc ttc aac aag      1672
Cys Gly Ile Leu Val Val Ala Leu Pro Ile Thr Ile Ile Phe Asn Lys
        395                 400                 405

ttt tcc aag tac tac cag aag cag aaa gac atg gaa gtg gac cag tgc      1720
Phe Ser Lys Tyr Tyr Gln Lys Gln Lys Asp Met Glu Val Asp Gln Cys
    410                 415                 420

agc gag gac cca cca gag aag tgc cat gag cta ccg tac ttt aac att      1768
Ser Glu Asp Pro Pro Glu Lys Cys His Glu Leu Pro Tyr Phe Asn Ile
425                 430                 435                 440

agg gac gtt tat gca cag caa gta cat gcc ttc atc acc agt ctg tct      1816
Arg Asp Val Tyr Ala Gln Gln Val His Ala Phe Ile Thr Ser Leu Ser
                445                 450                 455

tcc att ggc atc gtg gtc agt gat cct gac tcc aca gat gct tcg agc      1864
Ser Ile Gly Ile Val Val Ser Asp Pro Asp Ser Thr Asp Ala Ser Ser
            460                 465                 470

gtt gaa gac aat gag gat gct tac aac act gca tcc ctg gag aac tgt      1912
Val Glu Asp Asn Glu Asp Ala Tyr Asn Thr Ala Ser Leu Glu Asn Cys
        475                 480                 485

act gga aaa tga gcaggggcat ttgcacagat atctcgtgtc ccttcctgac          1964
Thr Gly Lys
    490

attaggttaa cacagcttta taaacctcaa tgggtttgtt caaaaaatca tttaattctc   2024

agggtgtacc ttttagccat agttggacat tcattgctga attctgaaat gatagaatta   2084

tctttatttt tctcagtgag atcaattaaa atgccttgtt ctgaaattta ttttttacaa   2144

gagagagttg taatacggtt ttttggggaa aaaagtaaat gatattggga aggatttatt   2204

gctacggctt acgcatcatt ctatatttgc cattcactca cattgagcta actataaatt   2264

actgatgata gagcagaggc ccagctgact gaagatgacg acatgcatgt aagatctaca   2324

acatgagaca atgcatgtaa atccatgttc atgttccaga catgggaatt aggagcccaa   2384

taaacttcta atttggtatg gagaaaaaaa aaaaaaaaag ggcggccgct ctagaggatc   2444

cctcgagggg cccaagctta cgcgtgcatg cracgtcata ccncnctccc              2494


<210> SEQ ID NO 7
<211> LENGTH: 491
<212> TYPE: PRT
<213> ORGANISM: Mus musculus

<400> SEQUENCE: 7

Met Val Phe Gly Glu Phe Phe His Arg Pro Gly Gln Asp Glu Glu Leu
 1               5                  10                  15

Val Asn Leu Asn Val Gly Gly Phe Lys Gln Ser Val Asp Gln Ser Thr
            20                  25                  30

Leu Leu Arg Phe Pro His Thr Arg Leu Gly Lys Leu Leu Thr Cys His
        35                  40                  45

Ser Glu Glu Ala Ile Leu Glu Leu Cys Asp Asp Tyr Ser Val Ala Asp
    50                  55                  60
```

-continued

```
Lys Glu Tyr Tyr Phe Asp Arg Asn Pro Phe Leu Phe Arg Tyr Val Leu
65                  70                  75                  80

Asn Phe Tyr Tyr Thr Gly Lys Leu His Val Met Glu Glu Leu Cys Val
                85                  90                  95

Phe Ser Phe Cys Gln Glu Ile Glu Tyr Trp Gly Ile Asn Glu Leu Phe
            100                 105                 110

Ile Asp Ser Cys Cys Ser Ser Arg Tyr Gln Glu Arg Lys Glu Glu Ser
        115                 120                 125

His Asp Lys Asp Trp Asp Gln Lys Ser Asn Asp Val Ser Thr Asp Ser
    130                 135                 140

Ser Phe Glu Glu Ser Ser Leu Phe Glu Lys Glu Leu Glu Lys Phe Asp
145                 150                 155                 160

Glu Leu Arg Phe Gly Gln Leu Arg Lys Lys Ile Trp Ile Arg Met Glu
                165                 170                 175

Asn Pro Ala Tyr Cys Leu Ser Ala Lys Leu Ile Ala Ile Ser Ser Leu
            180                 185                 190

Ser Val Val Leu Ala Ser Ile Val Ala Met Cys Val His Ser Met Ser
        195                 200                 205

Glu Phe Gln Asn Glu Asp Gly Glu Val Asp Asp Pro Val Leu Glu Gly
    210                 215                 220

Val Glu Ile Ala Cys Ile Ala Trp Phe Thr Gly Glu Leu Ala Ile Arg
225                 230                 235                 240

Leu Val Ala Ala Pro Ser Gln Lys Lys Phe Trp Lys Asn Pro Leu Asn
                245                 250                 255

Ile Ile Asp Phe Val Ser Ile Ile Pro Phe Tyr Ala Thr Leu Ala Val
            260                 265                 270

Asp Thr Lys Glu Glu Glu Ser Glu Asp Ile Glu Asn Met Gly Lys Val
        275                 280                 285

Val Gln Ile Leu Arg Leu Met Arg Ile Phe Arg Ile Leu Lys Leu Ala
    290                 295                 300

Arg His Ser Val Gly Leu Arg Ser Leu Gly Ala Thr Leu Arg His Ser
305                 310                 315                 320

Tyr His Glu Val Gly Leu Leu Leu Leu Phe Leu Ser Val Gly Ile Ser
                325                 330                 335

Ile Phe Ser Val Leu Ile Tyr Ser Val Glu Lys Asp Glu His Lys Ser
            340                 345                 350

Ser Leu Thr Ser Ile Pro Ile Cys Trp Trp Trp Ala Thr Ile Ser Met
        355                 360                 365

Thr Thr Val Gly Tyr Gly Asp Thr His Pro Val Thr Leu Ala Gly Lys
    370                 375                 380

Ile Ile Ala Ser Thr Cys Ile Ile Cys Gly Ile Leu Val Val Ala Leu
385                 390                 395                 400

Pro Ile Thr Ile Ile Phe Asn Lys Phe Ser Lys Tyr Tyr Gln Lys Gln
                405                 410                 415

Lys Asp Met Glu Val Asp Gln Cys Ser Glu Asp Pro Pro Glu Lys Cys
            420                 425                 430

His Glu Leu Pro Tyr Phe Asn Ile Arg Asp Val Tyr Ala Gln Gln Val
        435                 440                 445

His Ala Phe Ile Thr Ser Leu Ser Ser Ile Gly Ile Val Val Ser Asp
    450                 455                 460

Pro Asp Ser Thr Asp Ala Ser Ser Val Glu Asp Asn Glu Asp Ala Tyr
465                 470                 475                 480
```

-continued

```
Asn Thr Ala Ser Leu Glu Asn Cys Thr Gly Lys
                485                 490


<210> SEQ ID NO 8
<211> LENGTH: 1273
<212> TYPE: DNA
<213> ORGANISM: Homo sapiens
<220> FEATURE:
<221> NAME/KEY: CDS
<222> LOCATION: (2)...(1273)

<400> SEQUENCE: 8

g tcg acc tgg att aga atg gag aat cca gcg tac tgc ctg tcc gct aag      49
  Ser Thr Trp Ile Arg Met Glu Asn Pro Ala Tyr Cys Leu Ser Ala
   1               5                  10                  15

ctt atc gct atc tcc tcc ttg agc gtg gtg ctg gcc tcc atc gtg gcc       97
Lys


atg tgc gtt cac agc atg tcg gag ttc cag aat gag gat gga gaa gtg      145
Leu Ile Ala Ile Ser Ser Leu Ser Val Val Leu Ala Ser Ile Val Ala
            20                  25                  30

gat gat ccg gtg ctg gaa gga gtg gag atc gcg tgc att gcc tgg ttc      193
Met Cys Val His Ser Met Ser Glu Phe Gln Asn Glu Asp Gly Glu Val
        35                  40                  45

acc ggg gag ctt gcc gtc cgg ctg gct gcc gct cct tgt caa aag aaa      241
Asp Asp Pro Val Leu Glu Gly Val Glu Ile Ala Cys Ile Ala Trp Phe
    50                  55                  60

ttc tgg aaa aac cct ctg aac atc att gac ttt gtc tct att att ccc      289
Thr Gly Glu Leu Ala Val Arg Leu Ala Ala Ala Pro Cys Gln Lys Lys
 65                  70                  75                  80

ttc tat gcc acg tcg acc tgg att aga atg gag aat cca gcg tac tgc      337
Phe Trp Lys Asn Pro Leu Asn Ile Ile Asp Phe Val Ser Ile Ile Pro
                85                  90                  95

ctg tcc gct aag ctt atc gct atc tcc tcc ttg agc gtg gtg ctg gcc      385
Phe Tyr Ala Thr Ser Thr Trp Ile Arg Met Glu Asn Pro Ala Tyr Cys
            100                 105                 110

tcc atc gtg gcc atg tgc gtt cac agc atg tcg gag ttc cag aat gag      433
Leu Ser Ala Lys Leu Ile Ala Ile Ser Ser Leu Ser Val Val Leu Ala
        115                 120                 125

gat gga gaa gtg gat gat ccg gtg ctg gaa gga gtg gag atc gcg tgc      481
Ser Ile Val Ala Met Cys Val His Ser Met Ser Glu Phe Gln Asn Glu
    130                 135                 140

att gcc tgg ttc acc ggg gag ctt gcc gtc cgg ctg gct gcc gct cct      529
Asp Gly Glu Val Asp Asp Pro Val Leu Glu Gly Val Glu Ile Ala Cys
145                 150                 155                 160

tgt caa aag aaa ttc tgg aaa aac cct ctg aac atc att gac ttt gtc      577
Ile Ala Trp Phe Thr Gly Glu Leu Ala Val Arg Leu Ala Ala Ala Pro
                165                 170                 175

tct att att ccc ttc tat gcc acg ttg ggc tgt aga cac caa gga gga      625
Cys Gln Lys Lys Phe Trp Lys Asn Pro Leu Asn Ile Ile Asp Phe Val
            180                 185                 190

aga gag gtg agg ata ttg aga aac atg ggc aag gtg gtc cag atc cta      673
Ser Ile Ile Pro Phe Tyr Ala Thr Leu Gly Cys Arg His Gln Gly Gly
        195                 200                 205

cgg ctt atg agg att ttc cga att cta aag ctt gcc cgg cac tcg gta      721
Arg Glu Val Arg Ile Leu Arg Asn Met Gly Lys Val Val Gln Ile Leu
    210                 215                 220

gga ctt cgg tct cta ggt gcc aca ctg aga cac agc tac cat gaa gtt      769
Arg Leu Met Arg Ile Phe Arg Ile Leu Lys Leu Ala Arg His Ser Val
225                 230                 235                 240

ggg ttt ctg ctt ctc ttc ctc tct gtg ggc att tcc att ttc tct gtg      817
```

-continued

```
Gly Leu Arg Ser Leu Gly Ala Thr Leu Arg His Ser Tyr His Glu Val
                245                 250                 255

ctt atc tac tcc gtg gag aaa gat gac cac aca tcc agc ctc acc agc      865
Gly Phe Leu Leu Leu Phe Leu Ser Val Gly Ile Ser Ile Phe Ser Val
            260                 265                 270

atc ccc atc tgc tgg tgg tgg gcc acc atc agc atg aca act gtg ggc      913
Leu Ile Tyr Ser Val Glu Lys Asp Asp His Thr Ser Ser Leu Thr Ser
        275                 280                 285

tat gga gac acc cac ccg gtc acc ttg gcg gga aag ctc atc gcc agc      961
Ile Pro Ile Cys Trp Trp Trp Ala Thr Ile Ser Met Thr Thr Val Gly
    290                 295                 300

aca tgc atc atc tgt ggc atc ttg gtg gtg gcc ctt ccc atc acc atc     1009
Tyr Gly Asp Thr His Pro Val Thr Leu Ala Gly Lys Leu Ile Ala Ser
305                 310                 315                 320

atc ttc aac aag ttt tcc aag tac tac cag aag caa aag gac att gat     1057
Thr Cys Ile Ile Cys Gly Ile Leu Val Val Ala Leu Pro Ile Thr Ile
                325                 330                 335

gtg gac cag tgc agt gag gat gca cca gag aag tgt cat gag cta cct     1105
Ile Phe Asn Lys Phe Ser Lys Tyr Tyr Gln Lys Gln Lys Asp Ile Asp
            340                 345                 350

tac ttt aac att agg gat ata tat gca cag cgg atg cac acc ttc att     1153
Val Asp Gln Cys Ser Glu Asp Ala Pro Glu Lys Cys His Glu Leu Pro
        355                 360                 365

acc agt ctc tct tct gta ggc att gtg gtg agc gat cct gac tcc aca     1201
Tyr Phe Asn Ile Arg Asp Ile Tyr Ala Gln Arg Met His Thr Phe Ile
    370                 375                 380

gat gct tca agc att gaa gac aat gag gac att tgt aac acc acc tcc     1249
Thr Ser Leu Ser Ser Val Gly Ile Val Val Ser Asp Pro Asp Ser Thr
385                 390                 395                 400

ttg gag aat tgc aca gca aaa tga                                      1273
Asp Ala Ser Ser Ile Glu Asp Asn Glu Asp Ile Cys Asn Thr Thr Ser
                405                 410                 415
```

```
<210> SEQ ID NO 9
<211> LENGTH: 423
<212> TYPE: PRT
<213> ORGANISM: Homo sapiens

<400> SEQUENCE: 9

Ser Thr Trp Ile Arg Met Glu Asn Pro Ala Tyr Cys Leu Ser Ala Lys
 1               5                  10                  15

Leu Ile Ala Ile Ser Ser Leu Ser Val Val Leu Ala Ser Ile Val Ala
            20                  25                  30

Met Cys Val His Ser Met Ser Glu Phe Gln Asn Glu Asp Gly Glu Val
        35                  40                  45

Asp Asp Pro Val Leu Glu Gly Val Glu Ile Ala Cys Ile Ala Trp Phe
    50                  55                  60

Thr Gly Glu Leu Ala Val Arg Leu Ala Ala Ala Pro Cys Gln Lys Lys
65                  70                  75                  80

Phe Trp Lys Asn Pro Leu Asn Ile Ile Asp Phe Val Ser Ile Ile Pro
                85                  90                  95

Phe Tyr Ala Thr Ser Thr Trp Ile Arg Met Glu Asn Pro Ala Tyr Cys
            100                 105                 110

Leu Ser Ala Lys Leu Ile Ala Ile Ser Ser Leu Ser Val Val Leu Ala
        115                 120                 125

Ser Ile Val Ala Met Cys Val His Ser Met Ser Glu Phe Gln Asn Glu
    130                 135                 140

Asp Gly Glu Val Asp Asp Pro Val Leu Glu Gly Val Glu Ile Ala Cys
```

-continued

```
145                 150                 155                 160

Ile Ala Trp Phe Thr Gly Glu Leu Ala Val Arg Leu Ala Ala Ala Pro
                165                 170                 175

Cys Gln Lys Lys Phe Trp Lys Asn Pro Leu Asn Ile Ile Asp Phe Val
            180                 185                 190

Ser Ile Ile Pro Phe Tyr Ala Thr Leu Gly Cys Arg His Gln Gly Gly
        195                 200                 205

Arg Glu Val Arg Ile Leu Arg Asn Met Gly Lys Val Val Gln Ile Leu
    210                 215                 220

Arg Leu Met Arg Ile Phe Arg Ile Leu Lys Leu Ala Arg His Ser Val
225                 230                 235                 240

Gly Leu Arg Ser Leu Gly Ala Thr Leu Arg His Ser Tyr His Glu Val
                245                 250                 255

Gly Phe Leu Leu Leu Phe Leu Ser Val Gly Ile Ser Ile Phe Ser Val
            260                 265                 270

Leu Ile Tyr Ser Val Glu Lys Asp Asp His Thr Ser Ser Leu Thr Ser
        275                 280                 285

Ile Pro Ile Cys Trp Trp Trp Ala Thr Ile Ser Met Thr Thr Val Gly
    290                 295                 300

Tyr Gly Asp Thr His Pro Val Thr Leu Ala Gly Lys Leu Ile Ala Ser
305                 310                 315                 320

Thr Cys Ile Ile Cys Gly Ile Leu Val Val Ala Leu Pro Ile Thr Ile
                325                 330                 335

Ile Phe Asn Lys Phe Ser Lys Tyr Tyr Gln Lys Gln Lys Asp Ile Asp
            340                 345                 350

Val Asp Gln Cys Ser Glu Asp Ala Pro Glu Lys Cys His Glu Leu Pro
        355                 360                 365

Tyr Phe Asn Ile Arg Asp Ile Tyr Ala Gln Arg Met His Thr Phe Ile
    370                 375                 380

Thr Ser Leu Ser Ser Val Gly Ile Val Val Ser Asp Pro Asp Ser Thr
385                 390                 395                 400

Asp Ala Ser Ser Ile Glu Asp Asn Glu Asp Ile Cys Asn Thr Thr Ser
                405                 410                 415

Leu Glu Asn Cys Thr Ala Lys
            420


<210> SEQ ID NO 10
<211> LENGTH: 17
<212> TYPE: PRT
<213> ORGANISM: Unknown
<220> FEATURE:
<223> OTHER INFORMATION: Consensus sequence

<400> SEQUENCE: 10

Gly Ile Leu Val Val Ala Leu Pro Ile Thr Ile Ile Phe Asn Lys Phe
 1               5                  10                  15

Ser


<210> SEQ ID NO 11
<211> LENGTH: 2266
<212> TYPE: DNA
<213> ORGANISM: Homo sapiens
<220> FEATURE:
<221> NAME/KEY: CDS
<222> LOCATION: (308)...(1783)

<400> SEQUENCE: 11
```

-continued

```
cgcgggcagg cggcgtcgca gagcggagct agctggatgc gtccggactc ctgcaggtga     60

gagtgatttt ccagtgattg ctttggcctg tacaaccaga gaacaggatt cttcccttct    120

ttttggccac caaatgccta tgtgcaccac acattccagt gtgctgagaa gggcagagct    180

tcttggatga tgatggacgt cccaccgggc aggatgaaag cagaacgtgt ggcatctcca    240

cctcaagggt gcagcctgat cttcctcttc tcccttgcca gccagcactc tgccttctgt    300

atccacc atg gtg ttt ggt gag ttt ttc cat cgc cct gga caa gac gag      349
        Met Val Phe Gly Glu Phe Phe His Arg Pro Gly Gln Asp Glu
          1               5                  10

gaa ctt gtc aac ctg aat gtg ggg ggc ttt aag cag tct gtt gac caa      397
Glu Leu Val Asn Leu Asn Val Gly Gly Phe Lys Gln Ser Val Asp Gln
 15                  20                  25                  30

agc acc ctc ctg cgg ttt cct cac acc aga ctg ggg aag ctg ctt act      445
Ser Thr Leu Leu Arg Phe Pro His Thr Arg Leu Gly Lys Leu Leu Thr
                 35                  40                  45

tgc cat tct gaa gag gcc att ctg gag ctg tgt gat gat tac agt gtg      493
Cys His Ser Glu Glu Ala Ile Leu Glu Leu Cys Asp Asp Tyr Ser Val
             50                  55                  60

gcc gat aag gaa tac tac ttt gat cgg aat ccc tcc ttg ttc aga tat      541
Ala Asp Lys Glu Tyr Tyr Phe Asp Arg Asn Pro Ser Leu Phe Arg Tyr
         65                  70                  75

gtt ttg aat ttt tat tac acg ggg aag ctg cat gtc atg gag gag ctg      589
Val Leu Asn Phe Tyr Tyr Thr Gly Lys Leu His Val Met Glu Glu Leu
     80                  85                  90

tgc gta ttc tca ttc tgc cag gag atc gag tac tgg ggc atc aac gag      637
Cys Val Phe Ser Phe Cys Gln Glu Ile Glu Tyr Trp Gly Ile Asn Glu
 95                 100                 105                 110

ctc ttc att gat tct tgc tgc agc aat cgc tac cag gaa cgc aag gag      685
Leu Phe Ile Asp Ser Cys Cys Ser Asn Arg Tyr Gln Glu Arg Lys Glu
                115                 120                 125

gaa aac cac gag aag gac tgg gac cag aaa agc cat gat gtg agt acc      733
Glu Asn His Glu Lys Asp Trp Asp Gln Lys Ser His Asp Val Ser Thr
            130                 135                 140

gac tcc tcg ttt gaa gag tcg tct ctg ttt gag aaa gag ctg gag aag      781
Asp Ser Ser Phe Glu Glu Ser Ser Leu Phe Glu Lys Glu Leu Glu Lys
        145                 150                 155

ttt gac aca ctg cga ttt ggt cag ctc cgg aag aaa atc tgg att aga      829
Phe Asp Thr Leu Arg Phe Gly Gln Leu Arg Lys Lys Ile Trp Ile Arg
    160                 165                 170

atg gag aat cca gcg tac tgc ctg tcc gct aag ctt atc gct atc tcc      877
Met Glu Asn Pro Ala Tyr Cys Leu Ser Ala Lys Leu Ile Ala Ile Ser
175                 180                 185                 190

tcc ttg agc gtg gtg ctg gcc tcc atc gtg gcc atg tgc gtt cac agc      925
Ser Leu Ser Val Val Leu Ala Ser Ile Val Ala Met Cys Val His Ser
                195                 200                 205

atg tcg gag ttc cag aat gag gat gga gaa gtg gat gat ccg gtg ctg      973
Met Ser Glu Phe Gln Asn Glu Asp Gly Glu Val Asp Asp Pro Val Leu
            210                 215                 220

gaa gga gtg gag atc gcg tgc att gcc tgg ttc acc ggg gag ctt gcc     1021
Glu Gly Val Glu Ile Ala Cys Ile Ala Trp Phe Thr Gly Glu Leu Ala
        225                 230                 235

gtc cgg ctg gct gcc gct cct tgt caa aag aaa ttc tgg aaa aac cct     1069
Val Arg Leu Ala Ala Ala Pro Cys Gln Lys Lys Phe Trp Lys Asn Pro
    240                 245                 250

ctg aac atc att gac ttt gtc tct att att ccc ttc tat gcc acg ttg     1117
Leu Asn Ile Ile Asp Phe Val Ser Ile Ile Pro Phe Tyr Ala Thr Leu
255                 260                 265                 270

gct gta gac acc aag gag gaa gag agt gag gat att gag aac atg ggc     1165
```

-continued

```
Ala Val Asp Thr Lys Glu Glu Glu Ser Glu Asp Ile Glu Asn Met Gly
                275                 280                 285

aag gtg gtc cag atc cta cgg ctt atg agg att ttc cga att cta aag      1213
Lys Val Val Gln Ile Leu Arg Leu Met Arg Ile Phe Arg Ile Leu Lys
            290                 295                 300

ctt gcc cgg cac tcg gta gga ctt cgg tct cta ggt gcc aca ctg aga      1261
Leu Ala Arg His Ser Val Gly Leu Arg Ser Leu Gly Ala Thr Leu Arg
        305                 310                 315

cac agc tac cat gaa gtt ggg ctt ctg ctt ctc ttc ctc tct gtg ggc      1309
His Ser Tyr His Glu Val Gly Leu Leu Leu Leu Phe Leu Ser Val Gly
    320                 325                 330

att tcc att ttc tct gtg ctt atc tac tcc gtg gag aaa gat gac cac      1357
Ile Ser Ile Phe Ser Val Leu Ile Tyr Ser Val Glu Lys Asp Asp His
335                 340                 345                 350

aca tcc agc ctc acc agc atc ccc atc tgc tgg tgg tgg gcc acc atc      1405
Thr Ser Ser Leu Thr Ser Ile Pro Ile Cys Trp Trp Trp Ala Thr Ile
                355                 360                 365

agc atg aca act gtg ggc tat gga gac acc cac ccg gtc acc ttg gcg      1453
Ser Met Thr Thr Val Gly Tyr Gly Asp Thr His Pro Val Thr Leu Ala
            370                 375                 380

gga aag ctc atc gcc agc aca tgc atc atc tgt ggc atc ttg gtg gtg      1501
Gly Lys Leu Ile Ala Ser Thr Cys Ile Ile Cys Gly Ile Leu Val Val
        385                 390                 395

gcc ctt ccc atc acc atc atc ttc aac aag ttt tcc aag tac tac cag      1549
Ala Leu Pro Ile Thr Ile Ile Phe Asn Lys Phe Ser Lys Tyr Tyr Gln
    400                 405                 410

aag caa aag gac att gat gtg gac cag tgc agt gag gat gca cca gag      1597
Lys Gln Lys Asp Ile Asp Val Asp Gln Cys Ser Glu Asp Ala Pro Glu
415                 420                 425                 430

aag tgt cat gag cta cct tac ttt aac att agg gat ata tat gca cag      1645
Lys Cys His Glu Leu Pro Tyr Phe Asn Ile Arg Asp Ile Tyr Ala Gln
                435                 440                 445

cgg atg cac acc ttc att acc agt ctc tct tct gta ggc att gtg gtg      1693
Arg Met His Thr Phe Ile Thr Ser Leu Ser Ser Val Gly Ile Val Val
            450                 455                 460

agc gat cct gac tcc aca gat gct tca agc att gaa gac aat gag gac      1741
Ser Asp Pro Asp Ser Thr Asp Ala Ser Ser Ile Glu Asp Asn Glu Asp
        465                 470                 475

att tgt aac acc acc tcc ttg gag aat tgc aca gca aaa tga              1783
Ile Cys Asn Thr Thr Ser Leu Glu Asn Cys Thr Ala Lys
    480                 485                 490

gcgggggtgt ttgtgcctgt ttctcttatc ctttcccgac attaggttaa cacagcttta    1843

taaacctcag tgggttcgtt aaaatcattt aattctcagg gtgtaccttt cagccatagt    1903

tggacattca ttgctgaatt ctgaaatgat agaattgtct ttatttttct ctgtgaggtc    1963

aattaaatgc cttgttctga aatttatttt ttacaagaga gagttgtgat atagtttgga    2023

atataagata aatggtattg ggtggggttt gtggctacag cttatgcatc attctgtgtt    2083

tgtcatttac tcacattgag ctaactttaa attactgaca agtagaatca aaggtgcagc    2143

tgactgagac gacatgcatg taagatccac aaaatgagac aatgcatgta aatccatgct    2203

catgttctaa acatggaaac taggagccta ataaacttcc taattcaaaa aaaaaaaaaa    2263

aaa                                                                   2266

<210> SEQ ID NO 12
<211> LENGTH: 491
<212> TYPE: PRT
<213> ORGANISM: Homo sapiens
```

-continued

<400> SEQUENCE: 12

```
Met Val Phe Gly Glu Phe Phe His Arg Pro Gly Gln Asp Glu Glu Leu
 1               5                  10                  15

Val Asn Leu Asn Val Gly Gly Phe Lys Gln Ser Val Asp Gln Ser Thr
            20                  25                  30

Leu Leu Arg Phe Pro His Thr Arg Leu Gly Lys Leu Leu Thr Cys His
        35                  40                  45

Ser Glu Glu Ala Ile Leu Glu Leu Cys Asp Asp Tyr Ser Val Ala Asp
    50                  55                  60

Lys Glu Tyr Tyr Phe Asp Arg Asn Pro Ser Leu Phe Arg Tyr Val Leu
65                  70                  75                  80

Asn Phe Tyr Tyr Thr Gly Lys Leu His Val Met Glu Glu Leu Cys Val
                85                  90                  95

Phe Ser Phe Cys Gln Glu Ile Glu Tyr Trp Gly Ile Asn Glu Leu Phe
            100                 105                 110

Ile Asp Ser Cys Cys Ser Asn Arg Tyr Gln Glu Arg Lys Glu Glu Asn
        115                 120                 125

His Glu Lys Asp Trp Asp Gln Lys Ser His Asp Val Ser Thr Asp Ser
    130                 135                 140

Ser Phe Glu Glu Ser Ser Leu Phe Glu Lys Glu Leu Glu Lys Phe Asp
145                 150                 155                 160

Thr Leu Arg Phe Gly Gln Leu Arg Lys Lys Ile Trp Ile Arg Met Glu
                165                 170                 175

Asn Pro Ala Tyr Cys Leu Ser Ala Lys Leu Ile Ala Ile Ser Ser Leu
            180                 185                 190

Ser Val Val Leu Ala Ser Ile Val Ala Met Cys Val His Ser Met Ser
        195                 200                 205

Glu Phe Gln Asn Glu Asp Gly Glu Val Asp Asp Pro Val Leu Glu Gly
    210                 215                 220

Val Glu Ile Ala Cys Ile Ala Trp Phe Thr Gly Glu Leu Ala Val Arg
225                 230                 235                 240

Leu Ala Ala Ala Pro Cys Gln Lys Lys Phe Trp Lys Asn Pro Leu Asn
                245                 250                 255

Ile Ile Asp Phe Val Ser Ile Ile Pro Phe Tyr Ala Thr Leu Ala Val
            260                 265                 270

Asp Thr Lys Glu Glu Glu Ser Glu Asp Ile Glu Asn Met Gly Lys Val
        275                 280                 285

Val Gln Ile Leu Arg Leu Met Arg Ile Phe Arg Ile Leu Lys Leu Ala
    290                 295                 300

Arg His Ser Val Gly Leu Arg Ser Leu Gly Ala Thr Leu Arg His Ser
305                 310                 315                 320

Tyr His Glu Val Gly Leu Leu Leu Leu Phe Leu Ser Val Gly Ile Ser
                325                 330                 335

Ile Phe Ser Val Leu Ile Tyr Ser Val Glu Lys Asp Asp His Thr Ser
            340                 345                 350

Ser Leu Thr Ser Ile Pro Ile Cys Trp Trp Trp Ala Thr Ile Ser Met
        355                 360                 365

Thr Thr Val Gly Tyr Gly Asp Thr His Pro Val Thr Leu Ala Gly Lys
    370                 375                 380

Leu Ile Ala Ser Thr Cys Ile Ile Cys Gly Ile Leu Val Val Ala Leu
385                 390                 395                 400

Pro Ile Thr Ile Ile Phe Asn Lys Phe Ser Lys Tyr Tyr Gln Lys Gln
                405                 410                 415
```

-continued

```
Lys Asp Ile Asp Val Asp Gln Cys Ser Glu Asp Ala Pro Glu Lys Cys
            420                 425                 430

His Glu Leu Pro Tyr Phe Asn Ile Arg Asp Ile Tyr Ala Gln Arg Met
        435                 440                 445

His Thr Phe Ile Thr Ser Leu Ser Ser Val Gly Ile Val Val Ser Asp
    450                 455                 460

Pro Asp Ser Thr Asp Ala Ser Ser Ile Glu Asp Asn Glu Asp Ile Cys
465                 470                 475                 480

Asn Thr Thr Ser Leu Glu Asn Cys Thr Ala Lys
                485                 490
```

POTASSIUM CHANNEL SUBUNIT POLYPEPTIDE AND POLYNUCLEOTIDE COMPOSITIONS AND USES THEREFOR

This application claims priority to U.S. Provisional Patent Application Serial No. 60/063,450 filed Oct. 29, 1997, which is herein incorporated by reference.

FIELD OF THE INVENTION

This invention relates to potassium channel subunit polypeptide and polynucleotide compositions, to the production of these compositions, and to the use of the compositions in the diagnosis, prevention, and treatment of disease.

BACKGROUND OF THE INVENTION

Potassium channels are a heterogeneous group of ion channels that allow selective permeation of potassium ions across the plasma membrane, but differ in details of activation mechanism, voltage range of activity, and kinetic properties. (Hille, B. (1992) *Ionic Channels of Excitable Membranes*, 2nd Ed., Sinauer, Sunderland, Mass.; Latorre, R. and Miller, C. (1983) J. Memb. Biol. 7:11–30). They contribute to numerous physiological functions, for example, action potential repolarization, cardiac pacemaking, neuron bursting, muscle contraction, hormone secretion, vascular tone regulation, renal ion reabsorption, learning and memory, and cell growth and differentiation.

Voltage-gated potassium (Kv) channels are critical determinants of excitability in nerve and muscle cells, where they regulate impulse conduction, rhythmicity, and synaptic transmission. These channels form the largest and most diversified family of ion channels. At least six subfamilies of these channels have been identified: Kv1 (Shaker), Kv2 (Shab), Kv3 (Shaw), Kv4 (Shal), KvLQT and EAG. Such channels are formed by the association of channel subunits, either of the same subunit (forming homomeric channels) or of different subunits (forming heteromeric channels). Kv channel subunits are characterized structurally by the presence of six transmembrane domains (S1–S6), one of which is highly positively charged, and a pore region between S5 and S6.

Regulation of Kv channel function can occur by association of different Kv subunits, resulting in heteromeric Kv channels having different conductance properties. Electrically silent Kv subunits, which by themselves do not form active homomeric channels, can modulate the conductance properties of Kv channels by associating with electrically active Kv subunits. For example, electrically-silent Kv subunits Kv6.1 and Kv8.1 modulate the conductance properties of Kv2 (Shab) channels by associating with Kv2.1 and Kv2.2 subunits, forming heteromeric Kv channels with conductance properties differing from the homomeric Kv2.1 and Kv2.2 channels (Post, M. A., et al. (1996) FEBS Lett. 399:177–182; Salinas. M. et al. (1997) J. Biol. Chem. 272:8774–8780)

Potassium channels are associated with a variety of disease states. In some diseases and disorders, abnormal ion channels are believed to be causative factors, while other diseases appear to arise from inappropriate regulation of otherwise normal ion channels. Diseases believed to have a particular association with potassium channels include neurological, cardiovascular, musculoskeletal, and proliferative disorders.

Potassium channel proteins are useful targets for drug therapy in a variety of neurological and vascular disease conditions. One such neurological condition is epilepsy, fundamentally a disease of neuronal overexcitability, resulting from excessive and synchronous firing of a large population of neurons in the cerebral cortex. In addition, many other neuropsychiatric diseases are consequences of abnormal neuronal activity in the cerebral cortex. Ideally, it would be desirable to treat epilepsy and related neuropsychiatric conditions with compounds that act selectively on ion channels in the cerebral cortex, to reduce side effects related to more generalized effects on the patient's nervous system. To this end, it would be desirable to isolate, characterize, and recombinantly express human ion channel proteins (i) whose activities are related to neuronal excitability, and (ii) which are localized in the cerebral cortex.

A vascular condition associated with potassium ion current is pulmonary artery (PA) hypertension. Reduced voltage-dependent potassium current in PA smooth muscle cells leads to PA vasoconstriction, pulmonary hypertension and heart failure. It would therefore be desirable to treat pulmonary hypertension with compounds that restore potassium current in PA smooth muscle. Furthermore, it has been demonstrated that the appetite suppressant fenfluramine, which potentiates serotonin release in the brain, inhibits vascular smooth muscle potassium currents and is a causative agent in pulmonary hypertension (Weir E. K. et al. (1996) Circulation 94:2216–2220). It would therefore be desirable to isolate, characterize, and recombinantly express human ion channel proteins which are expressed in muscle tissues such as pulmonary artery smooth muscle, for use as a screening target to identify channel modulators useful in treating pulmonary hypertension and other cardiovascular and musculoskeletal disorders. Such channel proteins would also be useful in identifying compounds, such as serotonin release potentiators, which do not modulate such channels and thus lack hypertensive side-effects.

SUMMARY OF THE INVENTION

The invention includes proteins having sequence similarity to the Shab subfamily of voltage-gated potassium channel subunits and identified herein as Shab-like voltage-gated potassium channel subunits-1 and -2 (Kv-SL1 and Kv-SL2, and collectively as Kv-SL). The invention includes a substantially purified KV-SL protein having an amino acid sequence at least 85% identical to the sequence identified as SEQ ID NO:3 or SEQ ID NO:7 and which is capable of associating with one or more Kv subunits to form a Kv channel. In other embodiments, Kv-SL protein has a sequence at least 90% identical, preferably at least 95% identical to SEQ ID NO:3 or SEQ ID NO:7. In another embodiment, Kv-SL1 protein includes a portion between about amino acids 223 and 481 having a sequence selected from the group consisting of (a) the sequence between amino acids 223 and 481 of SEQ ID NO:3, (b) the sequence SEQ ID NO:5, and (c) internally consistent variations between sequences (a) and (b). In another embodiment, Kv-SL2 protein includes a portion between about amino acids 170 and 491 having a sequence selected from the group consisting of (a) the sequence between amino acids 170 and 491 of SEQ ID NO:7, (b) the sequence SEQ ID NO:9, and (c) internally consistent variations between sequences (a) and (b). In a more specific embodiment, Kv-SL1 protein has the sequence SEQ ID NO:3. In another specific embodiment, Kv-SL2 protein has the sequence SEQ ID NO:5 or SEQ ID NO:12. In another embodiment, Kv-SL protein is a human protein. The invention also includes fragments of Kv-SL protein, which are antigenic or which are capable of interacting with other proteins, peptides, or chemicals, such interaction which alters the functional properties or cellular/subcellular localization of Kv-SL protein or a Kv channel comprising Kv-SL. In one embodiment, the fragment corresponds to an intracellular domain of Kv-SL protein.

In another aspect the invention includes an isolated nucleic acid having a sequence which encodes Kv-SL as described above, or a sequence complementary to the Kv-SL coding sequence, and a composition comprising the nucleic acid. The nucleic acid may be mRNA, cRNA, DNA, cDNA, genomic DNA, or an antisense analog thereof. In various embodiments the nucleic acid may encode a Kv-SL protein having an amino acid sequence at least 85%, 90%, 95%, or 97% identical to SEQ ID NO:3 or SEQ ID NO:7. In another embodiment, the nucleic acid may encode a Kv-SL1 protein which includes a portion between about amino acids 223 and 481 having a sequence selected from the group consisting of (a) the sequence between amino acids 223 and 481 of SEQ ID NO:3, (b) the sequence SEQ ID NO:5, and (c) internally consistent variations between sequences (a) and (b). In another embodiment, the nucleic acid may encode a Kv-SL2 protein which includes a portion between about amino acids 170 and 491 having a sequence selected from the group consisting of (a) the sequence between amino acids 170 and 491 of SEQ ID NO:7, (b) the sequence SEQ ID NO:9, and (c) internally consistent variations between sequences (a) and (b). In more specific embodiments, the nucleic acid encodes a Kv-SL protein having the sequence SEQ ID NO:3, SEQ ID NO:5, or SEQ ID NO:12. In another embodiment, the nucleic acid encodes a human Kv-SL protein. In other embodiments, the nucleic acid has the sequence identified as SEQ ID NO:2, SEQ ID NO:6, SEQ ID NO:11, or the complement thereof.

The invention also contemplates polynucleotides at least 12 nucleotides in length, preferably at least 15 nucleotides in length, more preferably at least 20, 25, 30, or 50 nucleotides in length, which hybridize under at least high-stringency conditions to any of the Kv-SL nucleic acids described above. The polynucleotide may be mRNA, cRNA, DNA, cDNA, genomic DNA, or an antisense analog thereof.

Also disclosed is a recombinant expression vector containing a nucleic acid encoding Kv-SL as described above, and, operably linked to the polynucleotide, regulatory elements effective for expression of the protein in a selected host. Preferred coding sequences are given above. In a related aspect, the invention includes a host cell, preferably a eukaryotic host cell, containing the vector.

The invention further includes a method for producing Kv-SL by recombinant techniques, by culturing recombinant host cells containing a nucleic acid encoding Kv-SL under conditions promoting expression of the protein, and subsequent recovery of the protein from the host cell.

In still another aspect, the invention includes an antibody specific for Kv-SL. The antibody has diagnostic and therapeutic applications, particularly in treating neurological and cardiovascular disorders. Treatment methods which employ antisense or coding sequence polynucleotides for inhibiting or enhancing levels of Kv-SL are also contemplated, as are treatment methods which employ antibodies specific for Kv-SL.

Diagnostic methods for detecting levels of Kv-SL in specific tissue samples, and for detecting levels of expression of Kv-SL in tissues, also form part of the invention. In one embodiment, a method of detecting a polynucleotide which encodes Kv-SL in a biological sample, involves the steps of: (a) hybridizing a polynucleotide, which is capable of hybridizing to a polynucleotide which encodes Kv-SL, to nucleic acid material of a biological sample, thereby forming a hybridization complex, and (b) detecting the hybridization complex, wherein the presence of the complex correlates with the presence of the polynucleotide encoding Kv-SL in the biological sample. Methods for detecting mutations in the coding region of Kv-SL are also contemplated.

Screening methods which employ Kv-SL for identifying a candidate compound which modulates the activity of Kv-SL also form part of the invention. An exemplary method includes (a) contacting a test compound with Kv-SL, under conditions in which an activity of Kv-SL can be measured, (b) measuring the effect of the test compound on the activity of Kv-SL, and (c) identifying the test compound as a candidate compound if its effect on the activity of Kv-SL is above a selected threshold level. The activity measured may be, for example, potassium conductance in a eukaryotic cell which expresses recombinant Kv-SL. In one embodiment, Kv-SL is a subunit of a heteromeric Kv channel. In another embodiment, the test compound is a component of a combinatorial library. In another embodiment, the test compound is an antibody specific for Kv-SL.

Screening methods which employ Kv-SL for identifying a candidate compound which does not modulate Kv-SL, for the purpose of identifying therapeutic compounds lacking Kv-SL-associated effects, also form part of the invention. An exemplary method includes (a) contacting a test compound with Kv-SL, under conditions in which an activity of Kv-SL can be measured, (b) measuring the effect of the test compound on the activity of Kv-SL, and (c) identifying the test compound as Kv-SL negative if its effect on the activity of Kv-SL is below a selected threshold level. The activity measured may be, for example, potassium conductance in a eukaryotic cell which expresses recombinant Kv-SL. In one embodiment, Kv-SL is a subunit of a heteromeric Kv channel. In another embodiment, the test compound is a component of a combinatorial library. In another embodiment, the test compound is a serotonin reuptake inhibitor or a serotonin release stimulator.

The invention also includes, in a related aspect, a compound identified by the screening methods described above, including a purified agonist (for example, a "channel opener") and a purified antagonist (for example, a "channel blocker"). The invention further includes a purified antibody which specifically binds to a polypeptide described above.

The invention also includes methods to alter the expression level of Kv-SL by gene therapy techniques to achieve therapeutic benefit in patients.

These and other objects and features of the invention will become more fully apparent when the following detailed description is read in conjunction with the accompanying drawings.

BRIEF DESCRIPTION OF THE FIGURES

FIGS. 1A–1F show a nucleic acid sequence (SEQ ID NO:2) and deduced amino acid sequence (SEQ ID NO:3) of a full-length Kv-SL1 from mouse;

FIGS. 2A–2C show a nucleic acid sequence (SEQ ID NO:4) and deduced amino acid sequence (SEQ ID NO:5) of a portion of a Kv-SL1 from human;

FIGS. 3A–3F show a nucleic acid sequence (SEQ ID NO:6) and deduced amino acid sequence (SEQ ID NO:7) of a full-length Kv-SL2 from mouse;

FIGS. 4A–4D show a nucleic acid sequence (SEQ ID NO:8) and deduced amino acid sequence (SEQ ID NO:9) of a portion of a Kv-SL2 from human; and FIGS. 5A–5C show a multiple amino acid sequence alignment of full-length mKv-SL1 (SEQ ID NO:3), a portion of hKv-SL1 (SEQ ID NO:5), full-length mKv-SL2 (SEQ ID NO:7), and a portion of hKv-SL2 (SEQ ID NO:9);

FIG. 6 is a pairwise amino acid sequence alignment of SEQ ID NO:3 and SEQ ID NO:5.

FIG. 7 is a pairwise amino acid sequence alignment of SEQ ID NO:7 and SEQ ID NO:9.

BRIEF DESCRIPTION OF THE SEQUENCES

SEQ ID NO:1 is the nucleic acid sequence of probe EST7760;

SEQ ID NO:2 is a nucleic acid sequence which encodes a full-length mouse Kv-SL1 (mKv-SL1);

SEQ ID NO:3 is the predicted translation product of SEQ ID NO:2;

SEQ ID NO:4 is a nucleic acid sequence which encodes a portion of hKv-SL1;

SEQ ID NO:5 is the predicted translation product of SEQ ID NO:4;

SEQ ID NO:6 is a nucleic acid sequence which encodes a full-length mKv-SL2;

SEQ ID NO:7 is the predicted translation product of SEQ ID NO:6;

SEQ ID NO:8 is a nucleic acid sequence which encodes a portion of hKv-SL2;

SEQ ID NO:9 is the predicted translation product of SEQ ID NO:8;

SEQ ID NO:10 corresponds to a region of Kv-SL corresponding to the putative S6 transmembrane segment and its adjacent region;

SEQ ID NO:11 is a nucleic acid sequence which encodes a full-length hKv-SL2; and SEQ ID NO:12 is the predicted translation product of SEQ ID NO:11.

DETAILED DESCRIPTION OF THE INVENTION

I. Definitions

Unless otherwise indicated, all terms used herein have the same meaning as they would to one skilled in the art of the present invention. Practitioners are particularly directed to Sambrook et al. (1989) Molecular Cloning: A Laboratory Manual (Second Edition), Cold Spring Harbor Press, Plainview, N.Y. and Ausubel FM et al. (1989) Current Protocols in Molecular Biology, John Wiley & Sons, New York, N.Y., for definitions and terms of the art. It is to be understood that this invention is not limited to the particular methodology, protocols, and reagents described, as these may vary.

The term "polypeptide" or "subunit" or "channel subunit", as used herein, refers to a compound made up of a single chain of amino acid residues linked by peptide bonds. The term "protein" as used herein may be synonymous with the term "polypeptide", or may refer, in addition, to a complex of two or more polypeptides.

A "channel" or "channel protein", as used herein, refers to a multisubunit protein comprising two or more P-domain-containing subunits, and may be formed of multimers of the same subunit (a "homomeric" channel) or of different subunits (a "heteromeric" channel). Channel proteins may contain "accessory subunits" which modulate the activity of the channel.

"Kv-SL" is a voltage-gated potassium channel subunit which contains a potential P-domain, six predicted transmembrane domains (S1–S6), and has at least 90%, preferably at least 95%, more preferably at least 97% sequence identity in the region corresponding to a portion of the Kv-SL putative S6 transmembrane segment and its adjacent region (SEQ ID NO:10).

"Kv-SL1" refers to a Kv-SL channel subunit having a sequence at least 85 percent, preferably at least 90 percent, and more preferably at least 95 percent identical to SEQ ID NO:3.

"Kv-SL2" refers to a Kv-SL channel subunit having a sequence at least 85 percent, preferably at least 90 percent, and more preferably at least 95 percent identical to SEQ ID NO:7.

The term "Kv-SL channel", as used herein, refers to a multimeric potassium channel, preferably of the Shab family, comprising at least one Kv-SL subunit.

The term "mature Kv-SL" refers to Kv-SL as it exists in the cell after post-translational processing; for example, after removal of a signal sequence.

The term "modified", when referring to a polypeptide of the invention, means a polypeptide which is modified either by natural processes, such as processing or other post-translational modifications, or by chemical modification techniques which are well known in the art. Among the numerous known modifications which may be present include, but are not limited to, acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

The term "biologically active" refers to a Kv-SL protein having structural, regulatory or biochemical functions of a naturally occurring Kv-SL protein including, but not limited to, the ability to effect or modulate potassium ion conductance when self-associated into a homomeric channel, or when associated with other Kv channel subunits into a heteromeric Kv channel. Likewise, "immunologically active" defines the capability of a natural, recombinant or synthetic Kv-SL, or any fragment thereof, to induce a specific immune response in appropriate animals or cells and to bind with specific antibodies.

The term "fragment," when referring to Kv-SL, means a polypeptide which has an amino acid sequence which is the same as part of but not all of the amino acid sequence of Kv-SL, which retains at least one of the functions or activities of Kv-SL, or which is capable of interacting with Kv-SL, other proteins, peptides, or other molecules, to alter a function or activity or the cellular/subcellular localization of a Kv-SL channel. Fragments contemplated include, but are not limited to, a Kv-SL fragment which retains the ability to bind a ligand of a Kv-SL channel, a Kv-SL fragment which blocks the binding of a ligand to a Kv-SL channel, or a Kv-SL fragment which retains immunological activity of Kv-SL (i.e., an antigenic fragment). The fragment preferably includes at least 10, more preferably at least 20, still more preferably at least 50, contiguous amino acid residues of Kv-SL.

The term "portion", when referring to a protein of the invention, means a polypeptide which has an amino acid sequence which is the same as part of the amino acid sequence of Kv-SL or a variant thereof, which does not necessarily retain any biological function or activity.

A "conservative substitution" refers to the substitution of an amino acid in one class by an amino acid in the same class, where a class is defined by common physicochemical amino acid sidechain properties and high substitution frequencies in homologous proteins found in nature (as determined, e.g., by a standard Dayhoff frequency exchange matrix or BLOSUM matrix). Six general classes of amino acid sidechains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

A "non-conservative substitution" refers to the substitution of an amino acid in one class with an amino acid from another class; for example, substitution of an Ala, a class II residue, with a class III residue such as Asp, Asn, Glu, or Gln.

"Optimal alignment" is defined as an alignment giving the highest percent identity score. Such alignment can be performed using a variety of commercially available sequence analysis programs, such as the local alignment program LALIGN using a ktup of 1, default parameters and the default PAM. A preferred alignment is the pairwise alignment using the CLUSTAL-W program in MacVector, operated with default parameters, including an open gap penalty of 10.0, an extended gap penalty of 0.1, and a BLOSUM30 similarity matrix.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two or more optimally aligned polypeptide sequences are identical. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence).

A first polypeptide region is said to "correspond" to a second polypeptide region when the regions are essentially co-extensive when the sequences containing the regions are aligned using a sequence alignment program, as above. Corresponding polypeptide regions typically contain a similar, if not identical, number of residues. It will be understood, however, that corresponding regions may contain insertions or deletions of residues with respect to one another, as well as some differences in their sequences.

A first polynucleotide region is said to "correspond" to a second polynucleotide region when the regions are essentially co-extensive when the sequences containing the regions are aligned using a sequence alignment program, as above. Corresponding polynucleotide regions typically contain a similar, if not identical, number of residues. It will be understood, however, that corresponding regions may contain insertions or deletions of bases with respect to one another, as well as some differences in their sequences.

The term "sequence identity" means nucleic acid or amino acid sequence identity in two or more aligned sequences, aligned as defined above.

"Sequence similarity" between two polypeptides is determined by comparing the amino acid sequence and its conserved amino acid substitutes of one polypeptide to the sequence of a second polypeptide. Thus, 80% protein sequence similarity means that 80% of the amino acid residues in two or more aligned protein sequences are conserved amino acid residues, i.e. are conservative substitutions.

"Hybridization" includes any process by which a strand of a nucleic acid joins with a complementary nucleic acid strand through base-pairing. Thus, strictly speaking, the term refers to the ability of the complement of the target sequence to bind to the test sequence, or vice-versa.

"Hybridization conditions" are based in part on the melting temperature (Tm) of the nucleic acid binding complex or probe and are typically classified by degree of "stringency" of the conditions under which hybridization is measured. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm of the probe. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. An example of "high stringency" conditions includes hybridization at about 68° C. and washing at about 50° C. in about 0.1×SSC/0.1% SDS.

The term "gene" as used herein means the segment of DNA involved in producing a polypeptide chain; it may include regions preceding and following the coding region, e.g. 5' untranslated (5' UTR) or "leader" sequences and 3' UTR or "trailer" sequences, as well as intervening sequences (introns) between individual coding segments (exons).

An "isolated polynucleotide having a sequence which encodes Kv-SL" is a polynucleotide which contains the coding sequence of Kv-SL (i) in isolation, (ii) in combination with additional coding sequences, such as fusion protein or signal peptide, in which the Kv-SL coding sequence is the dominant coding sequence, (iii) in combination with non-coding sequences, such as introns and control elements, such as promoter and terminator elements or 5' and/or 3' untranslated regions, effective for expression of the coding sequence in a suitable host, and/or (iv) in a vector or host environment in which the Kv-SL coding sequence is a heterologous gene.

The terms "heterologous DNA" and "heterologous RNA" refer to nucleotides that are not endogenous to the cell or part of the genome in which they are present; generally such nucleotides have been added to the cell, by transfection, microinjection, electroporation, or the like. Such nucleotides generally include at least one coding sequence, but this coding sequence need not be expressed.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The term "fragment," when referring to an Kv-SL nucleic acid, means a polynucleotide which has a sequence which is the same as part of but not all of the sequence of the Kv-SL nucleic acid sequence. A fragment preferably includes at least 12 contiguous bases of Kv-SL nucleic acid sequence.

The term "expression vector" refers to vectors that have the ability to incorporate and express heterologous DNA fragments in a foreign cell. Many prokaryotic and eukaryotic expression vectors are commercially available. Selection of appropriate expression vectors is within the knowledge of those having skill in the art.

The term "substantially purified" refers to molecules, either polynucleotides or polypeptides, that are removed from their natural environment, isolated or separated, and are at least 60% free, preferably 75% free, and most preferably 90% free from other components with which they are naturally associated.

A "variant" polynucleotide sequence may encode a "variant" amino acid sequence which is altered by one or more amino acids from the reference polypeptide sequence. The variant polynucleotide sequence may encode a variant amino acid sequence which contains "conservative" substitutions, wherein the substituted amino acid has structural or chemical properties similar to the amino acid which it replaces. In addition, or alternatively, the variant polynucleotide sequence may encode a variant amino acid sequence which contains "non-conservative" substitutions, wherein the substituted amino acid has dissimilar structural or chemical properties to the amino acid which it replaces. Variant polynucleotides may also encode variant amino acid sequences which contain amino acid insertions or deletions, or both. Furthermore, a variant polynucleotide may encode the same polypeptide as the reference polynucleotide sequence but, due to the degeneracy of the genetic code, has a polynucleotide sequence which is altered by one or more bases from the reference polynucleotide sequence.

An "allelic variant" is an alternate form of a polynucleotide sequence which may have a substitution, deletion or addition of one or more nucleotides, which does not substantially alter the function of the encoded polypeptide. "Alternative splicing" is a process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

"Splice variants" of Kv-SL, when referred to in the context of an mRNA transcript, are mRNAs produced by alternative splicing of coding regions, i.e., exons, from the Kv-SL gene.

"Splice variants" of Kv-SL, when referred to in the context of the protein itself, are Kv-SL translation products which are encoded by alternatively-spliced Kv-SL mRNA transcripts.

A "mutant" amino acid or polynucleotide sequence is a variant amino acid sequence, or a variant polynucleotide sequence which encodes a variant amino acid sequence, which has significantly altered biological activity from that of the naturally occurring protein.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring sequence.

A "substitution" results from the replacement of one or more nucleotides or amino acids by different nucleotides or amino acids, respectively.

The term "modulate" as used herein refers to the change in activity of the polypeptide of the invention. Modulation may relate to an increase or a decrease in biological activity, binding characteristics, or any other biological, functional, or immunological property of the molecule.

The term "agonist" as used herein, refers to a molecule which, when bound to the channel or subunit of the present invention, modulates the activity of the channel comprising said subunit by inducing, increasing, or prolonging the duration of the biological activity, e.g., the potassium ion flux, mediated by the channel. An agonist as used herein may also be referred to as a "channel opener". Agonists may themselves be polypeptides, nucleic acids, carbohydrates, lipids, or derivatives thereof, or any other ligand which binds to and modulates the activity of the channel.

The term "antagonist" as used herein, refers to a molecule which, when bound to the channel or the subunit of the present invention, modulates the activity of the channel comprising said subunit by blocking, decreasing, or shortening the duration of the biological activity, e.g., the potassium ion flux, mediated by the channel. An antagonist as used herein may also be referred to as a "channel blocker". Antagonists may themselves be polypeptides, nucleic acids, carbohydrates, lipids, or derivatives thereof, or any other ligand which binds to and modulates the activity of the channel.

The term "humanized antibody" refers to antibody molecule in which one or more amino acids have been replaced in the non-antigen binding regions in order to more closely resemble a human antibody, while still retaining the original binding activity of the antibody.

"Treating a disease" refers to administering a therapeutic substance effective to reduce the symptoms of the disease and/or lessen the severity of the disease.

II. Polynucleotides Encoding Kv-SL

The invention provides isolated Shab-like voltage-gated potassium channel subunits, referred to collectively as Kv-SL and individually as Kv-SL1 and Kv-SL2, and isolated polynucleotides encoding Kv-SL. As defined more fully in Section III below, Kv-SL is a member of the subfamily of voltage-gated potassium channel modulatory subunits having similarity to the Kv2 (Shab) channel, and has an amino acid sequence at least 85%, preferably at least 90%, more preferably at least 95%, most preferably at least 97% identical to the amino acid sequence identified as SEQ ID NO:3 or SEQ ID NO:7.

A1. Mouse Kv-SL

Polynucleotides encoding a mouse Kv-SL1 subunit and a mouse Kv-SL2 subunit were discovered in a mouse brain tissue cDNA library. Coding sequences were identified, cloned and sequenced substantially as described in Example 1. Briefly, a radiolabeled human probe EST7760 having the sequence SEQ ID NO:1 was used to screen cDNA molecules by filter hybridization. After secondary and tertiary screening with labeled probes, positive colonies were isolated, and the cDNA was subcloned and sequenced, resulting in the construction and identification of nucleic acids encoding full-length mouse Kv-SL1 and Kv-SL2, the nucleic acid sequences identified herein as SEQ ID NO:2 and SEQ ID NO:6, respectively.

The mKv-SL1 nucleic acid sequence SEQ ID NO:2 is 2799 nucleotides in length, with an open reading frame from nucleotides 154 to 1647, which encodes a polypeptide of 497 amino acids identified herein as SEQ ID NO:3. FIG. 1 shows the coding sequence and translation of mKv-SL1. The translated protein has a calculated molecular mass of approximately 55 kDal, and contains 6 putative transmembrane domains (S1–S6) spanning approximately amino acids 187 to 210 (S1), 244 to 263 (S2), 275 to 296 (S3), 312 to 334 (S4), 348 to 370 (S5), and 407 to 427 (S6), and a pore-forming "P-domain" spanning approximately amino acids 373 to 401.

The mKv-SL2 nucleic acid sequence SEQ ID NO:6 is 2494 nucleotides in length, and contains an open reading frame from nucleotides 449–1994 which encodes a polypeptide of 491 amino acids identified herein as SEQ ID NO:7. FIG. 3 shows the coding sequence and translation of mKv-SL2. The translated protein has a calculated molecular mass of approximately 56 kdal, and contains putative S1–S6 domains spanning approximately amino acids 183 to 206 (S1), 225 to 246 (S2), 256 to 277 (S3), 288 to 310 (S4), 328 to 346 (S5), and 386 to 406 (S6), and a P-domain spanning approximately amino acids 350 to 379.

A2. HumanKv-SL

Polynucleotides encoding human Kv-SL1 and Kv-SL2 were identified, cloned and sequenced employing methods similar to those described above by screening a human brain cDNA library as described in Example 2. This resulted in the initial identification of nucleic acids encoding portions of hKv-SL1 and hKv-SL2, the nucleic acid sequences identified herein as SEQ ID NO:4 and SEQ ID NO:8, respectively. Subsequent analysis resulted in the identification of nucleic acid identified herein as SEQ ID NO:11 which encodes a full-length hKv-SL2.

The hKv-SL1 nucleic acid sequence SEQ ID NO:4 is 774 nucleotides in length and encodes a 257 amino acid polypeptide identified herein as SEQ ID NO:5. FIG. 2 shows the coding sequence and translation of the partial hKv-SL1 coding sequence. The translated polypeptide aligns with 91% identity to amino acids 223–481 of mKv-SL1 (FIG. 6) and corresponds to an internal portion of Kv-SL1 comprising the S2 through S6 transmembrane domains and the P-domain, and a majority of the residues between S6 and the C-terminus.

The hKv-SL2 nucleic acid sequence SEQ ID NO:8 is 1273 nucleotides in length and encodes a 323 amino acid polypeptide identified herein as SEQ ID NO:9. FIG. 4 shows the coding sequence and translation of the partial hKv-SL2 coding sequence. The translated polypeptide aligns with 89% identity to amino acids 170–491 of mKv-SL2 (FIG. 7), and corresponds to the C-terminal portion of full-length Kv-SL2 comprising the S1 through S6 transmembrane domains and the P-domain, terminating at its stop codon.

A3. Expression Localization of Kv-SL

Expression localization of sequences encoding hKv-SL1 and hKv-SL2 channel subunits was examined by Northern analysis as described in Example 3. The results showed expression of hKv-SL1 was confined to the cerebral cortex areas of the brain, and, in particular, the temporal and occipital lobe areas of the cerebral cortex. Expression of hKv-SL2 was more widely distributed, with highest abundance in skeletal muscle, followed by pancreas, lung, placenta, brain, and heart, and with lower abundance in liver and kidney.

B. Polynucleotide Compositions

The polynucleotides of the invention include sequences which encode Kv-SL and sequences complementary to the coding sequence, and novel fragments of the polynucleotide. The polynucleotides may be in the form of RNA or in the form of DNA, and include mRNA, cRNA, synthetic RNA and DNA, cDNA, genomic DNA, and PNAs and other antisense RNA and DNA analogs. The polynucleotides may be double-stranded or single-stranded, and if single-stranded may be the coding strand or the non-coding (anti-sense, complementary) strand.

The polynucleotides may include the coding sequence of Kv-SL (i) in isolation, (ii) in combination with additional coding sequences, such as fusion protein or signal peptide, in which the Kv-SL coding sequence is the dominant coding sequence, (iii) in combination with non-coding sequences, such as introns and control elements, such as promoter and terminator elements or 5' and/or 3' untranslated regions, effective for expression of the coding sequence in a suitable host, and/or (iv) in a vector or host environment in which the Kv-SL coding sequence is a heterologous gene.

The polynucleotide may encode a polypeptide fragment of Kv-SL, e.g., an extracellular fragment, or an intracellular fragment, which has been cleaved from the transmembrane domain of the Kv-SL channel; for example, a fragment which retains the ability to bind a ligand of Kv-SL, or an antigenic fragment of Kv-SL.

The polynucleotides of the present invention may also have the protein coding sequence fused in-frame to a marker sequence which allows for purification of Kv-SL. The marker sequence may be, for example, a hexahistidine tag to provide for purification of the mature polypeptide fused to the marker in the case of a bacterial host, or, the marker sequence may be a hemagglutinin (HA) tag when a mammalian host, e.g. COS-7 cells, is used. The HA tag corresponds to an epitope derived from the influenza hemagglutinin protein (Wilson, I., et al. (1984) Cell 37:767).

Also contemplated are novel uses of polynucleotides, also referred to herein as oligonucleotides, typically having at least 12 bases, preferably at least 15, more preferably at least 20 or 30 bases, which hybridize under at least high stringency conditions to a Kv-SL nucleic acid sequence described above. The polynucleotides may be used as probes, primers, antisense agents, and the like, according to known methods.

C. Preparation of Polynucleotides

The polynucleotides may be obtained by screening cDNA libraries using oligonucleotide probes which can hybridize to or PCR-amplify polynucleotides which encode the Kv-SL and fragments disclosed above. cDNA libraries prepared from a variety of tissues are commercially available and procedures for screening and isolating cDNA clones are well-known to those of skill in the art. Such techniques are described in, for example, Sambrook et al. (1989) Molecular Cloning: A Laboratory Manual (2nd Edition), Cold Spring Harbor Press, Plainview, N.Y. and Ausubel FM et al. (1989) Current Protocols in Molecular Biology, John Wiley & Sons, New York, N.Y.

Hybridization conditions are based on the melting temperature (Tm) of the nucleic acid binding complex or probe and are typically classified by degree of "stringency" of the conditions under which hybridization is measured. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. An example of high stringency conditions includes hybridization at about 65° C. in about 5×SSPE and washing at about 65° C. in about 0.1×SSPE (where 1×SSPE=0.15 sodium chloride, 0.010 M sodium phosphate, and 0.001 M disodium EDTA).

The polynucleotides may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the RACE method using, for example, the MARATHON RACE kit (Cat. #K1 802-1; Clontech, Palo Alto, Calif.).

Alternatively, the technique of "restriction-site" PCR (Gobinda et al. (1993) PCR Methods Applic. 2:318–22), which uses universal primers to retrieve flanking sequence adjacent a known locus, may be employed. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al. (1988) Nucleic Acids Res 16:8186). The primers may be designed using OLIGO(R) 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Capture PCR (Lagerstrom M et al. (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker, JD et al. (1991; Nucleic Acids Res 19:3055–60). Additionally, one can use PCR, nested primers and PromoterFinder(TM) libraries to "walk in" genomic DNA (Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

The polynucleotides and oligonucleotides of the invention can also be prepared by solid-phase methods, according to known synthetic methods. Typically, fragments of up to about 100 bases are individually synthesized, then joined to form continuous sequences up to several hundred bases.

D. Applications of Polynucleotides

The polynucleotides and oligonucleotides of the invention have a variety of uses in (1) synthesis of Kv-SL, (2) diagnostics, (3) gene mapping, and (4) therapeutics.

D1. Synthesis of Kv-SL Proteins and Fragments

In accordance with the present invention, polynucleotide sequences which encode Kv-SL, splice variants, fragments of the protein, fusion proteins, or functional equivalents thereof, collectively referred to herein as "Kv-SL", may be used in recombinant DNA molecules that direct the expression of Kv-SL in appropriate host cells. Due to the inherent degeneracy of the genetic code, other nucleic acid sequences which encode substantially the same or a functionally equivalent amino acid sequence may be used to clone and express Kv-SL.

As will be understood by those of skill in the art, it may be advantageous to produce Kv-SL-encoding nucleotide sequences possessing non-naturally occurring codons. Codons preferred by a particular prokaryotic or eukaryotic host (Murray, E. et al. (1989) Nuc Acids Res 17:477–508) can be selected, for example, to increase the rate of Kv-SL polypeptide expression or to produce recombinant RNA transcripts having desirable properties, such as a longer half-life, than transcripts produced from naturally occurring sequence.

The polynucleotide sequences of the present invention can be engineered in order to alter a Kv-SL coding sequence for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns, to change codon preference, to produce splice variants, etc.

The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells which are genetically engineered with vectors of the invention, and the production of proteins and polypeptides of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the Kv-SL gene. The culture conditions, such as temperature, pH and the like, are those previously used with the host cell selected for expression, and will be apparent to those skilled in the art.

The polynucleotides of the present invention may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: LTR or SV40 promoter, the *E. coli* lac or trp promoter, the phage lambda PL promoter, and other promoters known to control expression of genes in prokaryotic or eukaryotic cells or their viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as described above, as well as an appropriate promoter or control sequence, may be employed to transform an appropriate host to permit the host to express the protein. Examples of appropriate expression hosts include: bacterial cells, such as *E. coli*, Streptomyces, and *Salmonella typhimurium*; fungal cells, such as yeast; insect cells such as Drosophila and Spodoptera Sf9; mammalian cells such as CHO, COS, BHK, HEK 293 or Bowes melanoma; adenoviruses; plant cells, etc. It is understood that not all cells or cell lines will be capable of producing fully functional Kv-SL; for example, antigenic fragments of Kv-SL may be produced in bacterial expression systems. The selection of an appropriate host is deemed to be within the scope of those skilled in the art from the teachings herein. The invention is not limited by the host cells employed.

In bacterial systems, a number of expression vectors may be selected depending upon the use intended for Kv-SL. For example, when large quantities of Kv-SL or fragments thereof are needed for the induction of antibodies, vectors which direct high level expression of fusion proteins that are readily purified may be desirable. Such vectors include, but are not limited to, multifunctional *E. coli* cloning and expression vectors such as Bluescript(R) (Stratagene), in which the Kv-SL coding sequence may be ligated into the vector in-frame with sequences for the amino-terminal Met and the subsequent 7 residues of beta-galactosidase so that a hybrid protein is produced; pIN vectors (Van Heeke & Schuster (1989) J Biol Chem 264:5503–5509); pET vectors (Novagen, Madison Wis.); and the like.

In the yeast *Saccharomyces cerevisiae* a number of vectors containing constitutive or inducible promoters such as alpha factor, alcohol oxidase and PGH may be used. For reviews, see Ausubel et al. (supra) and Grant et al. (1987; Methods in Enzymology 153:516–544).

In cases where plant expression vectors are used, the expression of a sequence encoding Kv-SL may be driven by any of a number of promoters. For example, viral promoters such as the 35S and 19S promoters of CaMV (Brisson et al. (1984) Nature 310:511–514) may be used alone or in combination with the omega leader sequence from TMV (Takamatsu et al. (1987) EMBO J 6:307–311). Alternatively, plant promoters such as the small subunit of RUBISCO (Coruzzi et al (1984) EMBO J 3:1671–1680; Broglie et al. (1984) Science 224:838–843); or heat shock promoters (Winter J and Sinibaldi RM (1991) Results. Probl. Cell Differ. 17:85–105) may be used. These constructs can be introduced into plant cells by direct DNA transformation or pathogen-mediated transfection. For reviews of such techniques, see Hobbs S or Murry LE (1992) in McGraw Hill Yearbook of Science and Technology, McGraw Hill, New York, N.Y., pp 191–196; or Weissbach and Weissbach (1988) Methods for Plant Molecular Biology, Academic Press, New York, N.Y., pp 421–463.

Kv-SL may also be expressed in an insect system. In one such system, *Autographa californica* nuclear polyhedrosis virus (AcNPV) is used as a vector to express foreign genes in *Spodoptera frugiperda* Sf9 cells or in Trichoplusia larvae. The Kv-SL coding sequence is cloned into a nonessential region of the virus, such as the polyhedrin gene, and placed under control of the polyhedrin promoter. Successful insertion of Kv-SL coding sequence will render the polyhedrin gene inactive and produce recombinant virus lacking coat protein coat. The recombinant viruses are then used to infect *S. frugiperda* cells or Trichoplusia larvae in which Kv-SL is expressed (Smith et al. (1983) J Virol 46:584; Engelhard EK et al (1994) Proc Nat Acad Sci 91:3224–3227).

In mammalian host cells, a number of viral-based expression systems may be utilized. In cases where an adenovirus is used as an expression vector, a Kv-SL coding sequence may be ligated into an adenovirus transcription/translation complex consisting of the late promoter and tripartite leader sequence. Insertion in a nonessential E1 or E3 region of the viral genome will result in a viable virus capable of expressing Kv-SL in infected host cells (Logan and Shenk (1984) Proc Natl Acad Sci 81:3655–3659). In addition, transcription enhancers, such as the rous sarcoma virus (RSV) enhancer, may be used to increase expression in mammalian host cells.

Specific initiation signals may also be required for efficient translation of a Kv-SL coding sequence. These signals include the ATG initiation codon and adjacent sequences. In cases where Kv-SL coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al. (1994) Results Probl Cell Differ 20:125–62; Bittner et al. (1987) Methods in Enzymol 153:516–544).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology). Cell-free translation systems can also be employed to produce polypeptides using RNAs derived from the DNA constructs of the present invention. Kv-SL mRNA or cRNA may also be microinjected into, e.g. *Xenopus laevis* oocytes, for production of Kv-SL for electrophysiological measurements or other assays.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, BHK, MDCK, 293, WI38, etc. have specific cellular machinery and characteristic mechanisms for such post-translational activities and may be chosen to ensure the correct modification and processing of the introduced, foreign protein. For practicing certain aspects of the invention, such as electrophysiological measurements described below, it is appreciated that it may be desirable that the host cell lack endogenous functionally expressed potassium channels having current characteristics similar to those exhibited by the Kv-SL protein described herein.

For long-term, high-yield production of recombinant proteins, stable expression is preferred. For example, cell lines which stably express Kv-SL may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Host cells transformed with a nucleotide sequence encoding KV-SL may be cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding Kv-SL can be designed with signal sequences which direct secretion of Kv-SL polypeptide through a prokaryotic or eukaryotic cell membrane.

Kv-SL may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a protease-cleavable polypeptide linker sequence between the purification domain and Kv-SL is useful to facilitate purification. One such expression vector provides for expression of a fusion protein compromising Kv-SL (e.g., a soluble Kv-SL fragment) fused to a polyhistidine region separated by an enterokinase cleavage site. The histidine residues facilitate purification on IMIAC (immobilized metal ion affinity chromatography, as described in Porath et al. (1992) Protein Expression and Purification 3:263–281) while the enterokinase cleavage site provides a means for isolating Kv-SL from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

Kv-SL can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. Finally, high performance liquid chromatography (HPLC) can be employed for final purification steps.

D2. Diagnostic Applications

The polynucleotides of the present invention may be used for a variety of diagnostic purposes. The polynucleotides may be used to detect and quantitate expression of Kv-SL in patient's cells, e.g. biopsied tissues, by detecting the presence of MRNA coding for Kv-SL. This assay typically involves obtaining total mRNA from the tissue and contacting the mRNA with a nucleic acid probe. The probe is a nucleic acid molecule of at least 12 nucleotides, preferably at least 20–30 nucleotides, capable of specifically hybridizing with a sequence included within the sequence of a nucleic acid molecule encoding Kv-SL under hybridizing conditions, detecting the presence of mRNA hybridized to the probe, and thereby detecting the expression of Kv-SL. This assay can be used to distinguish between absence, presence, and excess expression of Kv-SL and to monitor levels of Kv-SL expression during therapeutic intervention.

The invention also contemplates the use of the polynucleotides as a diagnostic for diseases resulting from inherited defective Kv-SL genes. These genes can be detected by comparing the sequences of the defective (i.e., mutant) Kv-SL gene with that of a normal one. Association of a mutant Kv-SL gene with abnormal Kv-SL activity may be verified. In addition, mutant Kv-SL genes can be inserted into a suitable vector for expression in a functional assay system as yet another means to verify or identify mutations. Once mutant genes have been identified, one can then screen populations of interest for carriers of the mutant gene.

Individuals carrying mutations in the gene of the present invention may be detected at the DNA level by a variety of techniques. Nucleic acids used for diagnosis may be obtained from a patient's cells, including but not limited to such as from blood, urine, saliva, placenta, tissue biopsy and autopsy material. Genomic DNA may be used directly for detection or may be amplified enzymatically by using PCR (Saiki, et al. (1986) Nature 324:163–166) prior to analysis. RNA or cDNA may also be used for the same purpose. As an example, PCR primers complementary to the nucleic acid of the present invention can be used to identify and analyze mutations in the gene of the present invention. Deletions and insertions can be detected by a change in size of the amplified product in comparison to the normal genotype.

Point mutations can be identified by hybridizing amplified DNA to radiolabeled RNA of the invention or alternatively, radiolabeled antisense DNA sequences of the invention. Sequence changes at specific locations may also be revealed by nuclease protection assays, such RNase and S1 protection or the chemical cleavage method (e.g. Cotton, et al. (1985) Proc. Natl. Acad. Sci. USA 85:4397–4401), or by differences in melting temperatures. “Molecular beacons” (Kostrikis L. G. et al. (1998) Science 279:1228–1229), hairpin-shaped, single-stranded synthetic oligonucleotides containing probe sequences which are complementary to the nucleic acid of the present invention, may also be used to detect point mutations or other sequence changes as well as monitor expression levels of Kv-SL. Such diagnostics would be particularly useful for, e.g., prenatal testing.

Another method for detecting mutations uses two DNA probes which are designed to hybridize to adjacent regions of a target, with abutting bases, where the region of known or suspected mutation(s) is at or near the abutting bases. The two probes may be joined at the abutting bases, e.g., in the presence of a ligase enzyme, but only if both probes are correctly base paired in the region of probe junction. The presence or absence of mutations is then detectable by the presence or absence of ligated probe.

Also suitable for detecting mutations in the Kv-SL coding sequence are oligonucleotide array methods based on sequencing by hybridization (SBH), as described, for example, in U.S. Pat. No. 5,547,839. In a typical method, the DNA target analyte is hybridized with an array of oligonucleotides formed on a microchip. The sequence of the target can then be “read” from the pattern of target binding to the array.

D3. Gene Mapping

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the Kv-SL cDNA. Computer analysis of the 3' untranslated region is used to rapidly select primers that do not span more than one exon in the genomic DNA, which would complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et aL (1988) Human Chromosomes: a Manual of Basic Techniques, Pergamon Press, New York.

Once a sequence has been mapped to a precise chromosomal location, the physical position of the sequence on the chromosome can be correlated with genetic map data. Such data are found, for example, in the OMIM database (Center for Medical Genetics, Johns Hopkins University, Baltimore, Md. and National Center for Biotechnology Information, National Library of Medicine, Bethesda, Md.). The OMIM gene map presents the cytogenetic map location of disease genes and other expressed genes. The OMIM database provides information on diseases associated with the chromosomal location. Such associations include the results of linkage analysis mapped to this interval, and the correlation of translocations and other chromosomal aberrations in this area with the advent of polygenic diseases, such as cancer.

D4. Therapeutic Applications

Polynucleotides which encode Kv-SL, or complements of the polynucleotides, may also be used for therapeutic purposes. Expression of KV-SL may be modulated through antisense technology, which controls gene expression through complementary polynucleotides, i.e. antisense DNA or RNA, to the control, 5' or regulatory regions of the gene encoding Kv-SL. For example, the 5' portion of the polynucleotide sequence which encodes the protein of the present invention is used to design an antisense oligonucleotide of from about 10 to 40 base pairs in length. Oligonucleotides derived from the transcription start site, e.g. between positions −10 and +10 from the start site, are preferred. An antisense DNA oligonucleotide is designed to be complementary to a region of the gene involved in transcription (Lee et al. (1979) Nucl. Acids Res. 6:3073; Cooney et al. (1988) Science 241:456; and Dervan et al. (1991) Science 251:1360), thereby preventing transcription and the production of Kv-SL. An antisense RNA oligonucleotide hybridizes to the mRNA in vivo and blocks translation of the mRNA molecule into Kv-SL protein (Okano (1991) J. Neurochem. 56:560). The antisense constructs can be delivered to cells by procedures known in the art such that the antisense RNA or DNA may be expressed in vivo.

The therapeutic polynucleotides of the invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The polypeptides, and agonist and antagonist compounds which are polypeptides, may also be employed in accordance with the present invention by expression of such polypeptides in vivo, which is often referred to as “gene therapy.” Cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, psi-2, psi-AM, PA12, T19-14X, VT-19-17-H2, psi-CRE, psi-CRIP, GP+E-86, GP+envAml2, and DAN cell lines as described in Miller (1990; Human Gene Therapy, Vol. 1, pg. 5–14). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

alignment, which shares 100% identity among the four Kv-SL sequences. This 17mer segment corresponds to the putative S6 transmembrane segment and its adjacent C-terminal region, and has the sequence identified herein as SEQ ID NO:10. Northern blot analysis shows sequences encoding Kv-SL1 were localized to cerebral cortex areas of the brain, and, in particular, the temporal and occipital lobe areas of the cerebral cortex. Kv-SL2 sequences were more widely distributed, with highest abundance in skeletal muscle, followed by pancreas, lung, placenta, brain, and heart, and with lower abundance in liver and kidney.

The substantially purified Kv-SL1 of the invention includes a protein having at least 85% sequence identity to SEQ ID NO:3, preferably at least 90%, more preferably at least 95% or 97% identity to SEQ ID NO:7. The substantially purified Kv-SL2 of the invention includes a protein having at least 85% sequence identity to SEQ ID NO:3, preferably at least 90%, more preferably at least 95% or 97% identity to SEQ ID NO:7. The protein may be a mammalian protein, preferably a human protein.

The invention also contemplates a substantially purified Kv-SL comprising a polypeptide having a sequence which is internally consistent with the mouse and human sequences identified above. For example, FIG. 6 shows an amino acid sequence alignment between mKv-SL1 (SEQ ID NO:3) and hKv-SL1 (SEQ ID NO:5) using the CLUSTAL-W (ver. 1.4) alignment program in pairwise mode, using the default pairwise alignment parameters (Open gap penalty=10.0, Extend gap penalty=0.1, and Blosum30 Similarity Matrix). FIG. 7 shows the corresponding alignment between mKv-SL2 (SEQ ID NO:7) and hKv-SL2 (SEQ ID NO:9). Reproduced below is part of the alignment shown in FIG. 6, corresponding to the alignment between amino acids 210–250 of SEQ ID NO:3 and amino acids 1–28 of SEQ ID NO:5:

```
SEQ ID NO:3 201ASIAAMCIHSLPEYQAREAAAAVAAVAAGRSAEEVRDDPVLRRLEYFCIA  250

SEQ ID NO:5   1                       VAAVAAGRSPEGVRDDPVLRRLEYFCIA   28
                                      ********* * ****************
```

The genes introduced into cells may be placed under the control of inducible promoters, such as the radiation-inducible Egr-1 promoter, (Maceri, H. J., et al. (1996) Cancer Res 56(19):4311), to stimulate Kv-SL production or antisense inhibition in response to radiation, e.g., radiation therapy for treating tumors.

III. Potassium Channel Subunit Kv-SL

A. Kv-SL Sequences

It is a discovery of the present invention that Kv-SL is an ion channel subunit. Hydrophobicity and sequence motif analysis of SEQ ID NO:3 and SEQ ID NO:7 indicate that Kv-SL contains six transmembrane domains and one pore-forming domain and is thus categorized as a 1P/6TM channel subunit. The invention is based in part on the sequence similarity between Kv-SL and other Shab-like voltage-gated potassium channels such as Kv2.1. The amino acid sequences of full-length mKv-SL1 (SEQ ID NO:3), partial hKv-SL1 (SEQ ID NO:5), full-length mKv-SL2 (SEQ ID NO:7), and partial hKv-SL2 (SEQ ID NO:9) were aligned using the CLUSTAL-W multiple sequence alignment program in MacVector™, with the results shown in FIG. 5. As shown, the four polypeptides have several regions of close sequence identity, particularly in the region corresponding to the positions designated 418–434 in the A polypeptide having a sequence which is an "internally consistent variation" between (a) the sequence between amino acids 223 and 250 of SEQ ID NO:3 and (b) the sequence between amino acids 1 and 28 of SEQ ID NO:5, would have the following sequence:

VAAVAAGRS(A/P)PE(E/G)GVRDDPVLRRLEYFCIA where (X/Y) indicates the presence of either amino acid X or amino acid Y at that position.

The present invention contemplates a substantially purified Kv-SL1 protein wherein the portion of said protein between about amino acids 223 and 481 has a sequence selected from the group consisting of (a) the sequence between amino acids 223 and 481 of SEQ ID NO:3, (b) the sequence SEQ ID NO:5, and (c) internally consistent variations between sequences (a) and (b).

The invention further contemplates a purified Kv-SL2 protein wherein the portion of said protein between about amino acids 170 and 491 has a sequence selected from the group consisting of (a) the sequence between amino acids 170 and 491 of SEQ ID NO:7, (b) the sequence SEQ ID NO:9, and (c) internally consistent variations between sequences (a) and (b).

The protein may be a recombinant protein, a natural protein or a synthetic protein, preferably a recombinant protein. The protein may be in mature and/or modified form, also as defined above. Also contemplated are protein fragments derived from Kv-SL, which are antigenic or which are capable of interacting with Kv-SL, or with other proteins, peptides, or other molecules, to alter a function or a biological activity of Kv-SL or the cellular/subcellular localization of Kv-SL.

The sequence variations may include those that are considered non-conservative substitutions, as defined above. Thus, for example, a protein with a sequence having at least 90% sequence identity with the protein identified as SEQ ID NO:3 (497 amino acid residues) contains up to 49 amino acid substitutions, preferably non-conservative substitutions. Kv-SL may be (i) a protein in which one or more of the amino acid residues in a sequence listed above are substituted with a non-conservative or non-conserved amino acid residue, or (ii) a protein in which one or more of the amino acid residues includes a substituent group, or (iii) a protein in which the Kv-SL is fused with another compound, such as a compound to increase the half-life of the protein (for example, polyethylene glycol (PEG)), or (iv) a protein in which additional amino acids are fused to Kv-SL, or (v) an isolated fragment of the protein which is soluble, i.e. not membrane bound, yet still binds its natural ligands. Such fragments, variants and derivatives are deemed to be within the scope of those skilled in the art from the teachings herein. In particular, splice variants of the channel are also contemplated.

B. Preparation of Kv-SL

Recombinant methods for producing and isolating Kv-SL and fragments are described above. In addition to recombinant production, fragments and portions of Kv-SL may be produced by direct peptide synthesis using solid-phase techniques (cf Stewart et al. (1969) Solid-Phase Peptide Synthesis, WH Freeman Co, San Francisco; Merrifield J (1963) J Am Chem Soc 85:2149–2154). In vitro peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Portions of Kv-SL may be chemically synthesized separately and combined using chemical methods.

The channel protein may also be obtained by isolation from natural sources, e.g., by. affinity purification using the anti-Kv-SL antibody described in the section below. Fragments corresponding to the extracellular regions and/or the intracellular regions of Kv-SL may be cleaved from the membrane-bound regions using limited proteolysis techniques known to those of skill in the art. The amino acid sequence of the fragment(s) so obtained may be used to design nucleotide coding sequence for recombinant production of the fragment(s).

C. Applications of Kv-SL

The Kv-SL subunit of.the invention has uses in (I) therapeutic treatment methods and (2) drug screening.

C1. Therapeutic Uses and Compositions

The Kv-SL subunit of the invention is generally useful in treating diseases and disorders associated with the actions of ion channels, including neurological, cardiovascular, and musculoskeletal disorders.

The conspicuous cortex-specific expression of human Kv-SL1 indicates that agonists which enhance the activity of hKv-SL1 will be useful in suppressing neuronal excitability in the cerebral cortex, and thus effective in treating epilepsy, and other neuropsychiatric conditions related to neuronal overexcitability. Therefore, compositions that modulate the activity of hKv-SL1, in particular, hKv-SL1 agonists, are expected to be useful for treating a wide range of neuropsychiatric diseases. Due to the highly restricted expression of hKv-SL1, therapies targeted to hKv-SL1 are likely to have fewer side-effects than, for example, existing anti-epilepsy drugs.

The expression of human Kv-SL2 in tissues and organs including muscle, heart, lung, and brain indicates that agonists which enhance the activity of hKv-SL2 will be useful in suppressing muscle contraction and vasoconstriction, and thus effective in treating disorders relating to myocyte depolarization such as pulmonary hypertension, heart disease, and in preventing heart attack and stroke. Therefore, compositions that modulate the activity of hKv-SL2, in particular, hKv-SL2 agonists, are expected to be useful for treating a wide range of cardiovascular and musculoskeletal diseases.

Kv-SL subunits of the present invention may associate with other Kv channel subunits, particularly Shab-like subunits such as Kv2 subunits, to form heteromeric Kv channels. Kv-SL may modulate the activity of Kv channels by such an association. Compositions which modulate Kv-SL contemplated by the invention include fragments of Kv-SL which are capable of interacting with Kv-SL, or with a Kv channel which comprises Kv-SL, such interaction which alters the functional properties or cellular/subcellular localization of Kv-SL or the Kv channel.

Compositions which modulate Kv-SL or associated Kv channels are tested in appropriate in vitro and in vivo animal models of disease, to confirm efficacy, tissue metabolism, and to estimate dosages, according to methods well known in the art.

Polypeptide compositions which modulate Kv-SL may be administered by any of a number of routes and methods designed to provide a consistent and predictable concentration of compound at the target organ or tissue. Polypeptide compositions may be administered alone or in combination with other agents, such as stabilizing compounds, and/or in combination with other pharmaceutical agents such as drugs or hormones.

Polypeptide compositions which modulate Kv-SL may be administered by a number of routes including, but not limited to oral, intravenous, intramuscular, transdermal, subcutaneous, topical, sublingual, or rectal means. Kv-SL compositions may also be administered via liposomes. Such administration routes and appropriate formulations are generally known to those of skill in the art.

For example, the polypeptide may be given topically to the skin or epithelial linings of body cavities, for infections in such regions. Examples of treatable body cavities include the vagina, the rectum and the urethra. Conveniently, the polypeptide would be formulated into suppository form for administration to these areas.

The polypeptide can be given via intravenous or intraperitoneal injection. Similarly, the polypeptide may be injected to other localized regions of the body. The polypeptide may also be administered via nasal insufflation. Enteral administration is also possible. For such administration, the polypeptide should be formulated into an appropriate capsule or elixir for oral administration, or into a suppository for rectal administration.

The foregoing exemplary administration modes will likely require that the polypeptides be formulated into an appropriate carrier, including ointments, gels, suppositories. Appropriate formulations are well known to persons skilled in the art.

Dosage of the polypeptide will vary, depending upon the potency and therapeutic index of the particular polypeptide selected. These parameters are easily determinable by the skilled practitioner. As an example, if the polypeptide inhibits neuronal cell degradation in vitro at a given concentration, the practitioner will know that the final desired therapeutic concentration will be this range, calculated on the basis of expected biodistribution. An appropriate target concentration is in the ng/kg to low mg/kg range, e.g., 50 ng/kg to 1 mg/kg body weight, for IV administration.

A therapeutic composition for use in the treatment method can include the polypeptide in a sterile injectable solution, the polypeptide in an oral delivery vehicle, or the polypeptide in a nebulized form, all prepared according to well known methods. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof.

C2. Screening Methods

The present invention also includes an assay for identifying molecules, such as synthetic drugs, antibodies, peptides, or other molecules, which have a modulating effect on the activity of the Kv-SL, e.g. agonists or antagonists of the Kv-SL of the present invention. Such an assay comprises the steps of providing a functional Kv-SL encoded by the polynucleotides of the present invention, contacting Kv-SL with one or more molecules to determine its modulating effect on the activity of the channel, and selecting from the molecules a candidate molecule capable of modulating Kv-SL channel activity. Such compounds are useful in the treatment of disease conditions associated with activation or depression of Kv-SL activity.

Kv-SL, its ligand-binding, catalytic, or immunogenic fragments, or oligopeptides thereof, can be used for screening therapeutic compounds in any of a variety of drug screening techniques. The protein employed in such a test may be membrane-bound, free in solution, affixed to a solid support, borne on a cell surface, or located intracellularly. The formation of binding complexes between Kv-SL and the agent being tested may be measured. Compounds which inhibit binding between Kv-SL and its agonists may also be measured.

In one embodiment, the screening system includes recombinantly expressed Kv-SL, and the compounds screened are tested for their ability to block or enhance the potassium channel modulation activity of Kv-SL. In a functional screening assay, mammalian cell lines which lack Kv-SL are used to express Kv-SL, either alone or together with other Kv channel subunits. In this assay, compounds are screened for their relative affinity as channel agonists (i.e., "openers") or antagonists (i.e., "blockers") by comparing the relative channel occupancy to the extent of ligand-induced stimulation or inhibition of potassium channel activity. Potassium channel activity, i.e. potassium ion conductance, may be measured as described in Example 4 or by other methods known to those of skill in the art.

Another technique for drug screening which may be used provides for high throughput screening of compounds having suitable binding affinity to the Kv-SL channel is described in detail by Geysen in PCT Application WO 84/03564, published on Sep. 13, 1984. In summary, large numbers of different small peptide test compounds are synthesized on a solid substrate, such as plastic pins or some other surface. The peptide test compounds are reacted with Kv-SL (as either a soluble extracellular fragment of Kv-SL, or intact Kv-SL solubilized in detergents or in lipid vesicles), and washed. Bound Kv-SL is then detected by methods well known in the art. Substantially purified Kv-SL can also be coated directly onto plates for use in the aforementioned drug screening techniques. Alternatively, non-neutralizing antibodies can be used to capture the peptide and immobilize it on a solid support.

Antibodies to Kv-SL, as described in Section IV. below, may also be used in screening assays according to methods well known in the art. For example, a "sandwich" assay may be performed, in which an anti-Kv-SL antibody is affixed to a solid surface such as a microtiter plate and solubilized Kv-SL or Kv-SL fragment is added. Such an assay can be used to capture compounds which bind to Kv-SL. Alternatively, such an assay may be used to measure the ability of compounds to interfere with the binding of a Kv-SL agonist to Kv-SL.

In general, it is first useful to determine whether the test compound has an acceptable toxicity profile, e.g., in a variety of in vitro cells and an animal model. It may also be useful to search the tested and identified compound(s) against existing compound databases to determine whether the compound or analogs thereof have been previously employed for pharmaceutical purposes, and if so, optimal routes of administration and dose ranges. Alternatively, or in addition, the compound can be tested against a battery of cells in vitro to generate a toxicity profile.

To optimize compound activity and/or specificity, it may be desirable to construct a library of near-neighbor analogs to search for analogs with greater Kv-SL specificity and/or activity. Methods for synthesizing near-neighbor and/or targeted compound libraries are well-known in the combinatorial library field.

With optimized compounds in hand, it is possible to define a compound pharmacophore, and further search existing pharmacophore databases, e.g., as provided by Tripos, to identify other compounds that may differ in 2-D structural formulae with the originally discovered compounds, but which share a common pharmacophore structure and activity.

Optimal doses and routes of administration of the test compounds may be deduced from information existing on analogs, or can be determined according to well known types of animal-model studies.

Efficacy and dosing can be established, for example, in a standard experimental animal seizure model, the DBA/2 audiogenic seizure model, which is used to evaluate compounds for anticonvulsive activity for potential use in epilepsy and other brain seizure disorders. Testing procedures in this model are detailed in Example 5. Briefly, a genetically seizure-prone strain of mice, DBA/2 mice (Jackson Laboratories, Bar Harbor, Maine), exhibit a reproducible pattern of seizure behaviors when exposed to a particular frequency and intensity of sound. Compounds with a wide variety of structures have been found to be active in this model, which is also independent of temperature (Jackson, H. C. and Scheideler, M. A. (1996) Psycho-pharmacology 126:85–90). This latter point is particularly important in the context of calcium channel blockers, which induce hypothermia, which is also anticonvulsant in many animals. Additional animal seizure models can also be employed, using methods that have been standardized in the art (Kupferberg, H. J. (1989) Epilepsia 30 (suppl. 1):S51–S56).

IV. Anti-Kv-SL Antibodies

In still another aspect of the invention, purified Kv-SL is used to produce anti-Kv-SL antibodies which have diagnostic and therapeutic uses related to the activity, distribution, and expression of Kv-SL.

Antibodies to Kv-SL may be generated by methods well known in the art. Such antibodies may include, but are not limited to, polyclonal, monoclonal, chimeric, humanized, single chain, Fab fragments and fragments produced by an Fab expression library. Antibodies, i.e., those which block ligand binding, are especially preferred for therapeutic use.

Kv-SL for antibody induction does not require biological activity; however, the protein fragment or oligopeptide must be antigenic. Peptides used to induce specific antibodies may have an amino acid sequence consisting of at least 10 amino acids, preferably at least 15 or 20 amino acids. Preferably they should mimic a portion of the amino acid sequence of the natural protein and may contain the entire amino acid sequence of a small, naturally occurring molecule. Short stretches of a Kv-SL polypeptide may be fused with another protein such as keyhole limpet hemocyanin and antibody produced against the chimeric molecule. Procedures well known in the art can be used for the production of antibodies to Kv-SL.

For the production of antibodies, various hosts including goats, rabbits, rats, mice, etc may be immunized by injection with Kv-SL or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Monoclonal antibodies to Kv-SL may be prepared using any technique which provides for the production of antibody molecules by continuous cell lines in culture. These include but are not limited to the hybridoma technique originally described by Koehler and Milstein (1975; Nature 256:495–497), the human B-cell hybridoma technique (Kosbor et al. (1983) Immunol Today 4:72; Cote et al. (1983) Proc Natl Acad Sci 80:2026–2030) and the EBV-hybridoma technique (Cole, et al. (1984) Mol. Cell Biol. 62:109–120).

Techniques developed for the production of "chimeric antibodies", the splicing of mouse antibody genes to human antibody genes to obtain a molecule with appropriate antigen specificity and biological activity can also be used (Morrison et al. (1984) Proc Natl Acad Sci 81:6851–6855; Neuberger et al. (1984) Nature 312:604–608; Takeda et al. (1985) Nature 314:452–454). Alternatively, techniques described for the production of single chain antibodies (U.S. Pat. No. 4,946,778) can be adapted to produce single-chain antibodies specific for Kv-SL.

Antibodies may also be produced by inducing in vivo production in the lymphocyte population or by screening recombinant immunoglobulin libraries or panels of highly specific binding reagents as disclosed in Orlandi et al. (1989; Proc Natl Acad Sci 86:3833–3837), and Winter G and Milstein C (1991; Nature 349:293–299).

Antibody fragments which contain specific binding sites for Kv-SL may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse WD et al. (1989) Science 256:1275–1281).

A. Diagnostic Applications

A variety of protocols for competitive binding or immunoradiometric assays using either polyclonal or monoclonal antibodies with established specificities are well known in the art. Such immunoassays typically involve the formation of complexes between Kv-SL and its specific antibody and the measurement of complex formation. A two-site, monoclonal-based immunoassay utilizing monoclonal antibodies reactive to two noninterfering epitopes on Kv-SL is preferred, but a competitive binding assay may also be employed. These assays are described in Maddox DE et al. (1983, J Exp Med 158:1211).

Antibodies which specifically bind Kv-SL are useful for the diagnosis of conditions or diseases characterized by expression of Kv-SL. Alternatively, such antibodies may be used in assays to monitor patients being treated with Kv-SL, its agonists, or its antagonists. Diagnostic assays for Kv-SL protein include methods utilizing the antibody and a label to detect Kv-SL or its fragments in extracts of cells, tissues, or biological fluids such as sera. The proteins and antibodies of the present invention may be used with or without modification. Frequently, the proteins and antibodies will be labeled by joining them, either covalently or noncovalently, with a reporter molecule. A wide variety of reporter molecules are known in the art.

A variety of protocols for measuring Kv-SL, using either polyclonal or monoclonal antibodies specific for the respective protein, are known in the art. Examples include enzyme-inked immunosorbent assay (ELISA), radioimmunoassay (RIA), and fluorescent activated cell sorting (FACS). As noted above, a two-site, monoclonal-based immunoassay utilizing monoclonal antibodies reactive to two non-interfering epitopes on Kv-SL is preferred, but a competitive binding assay may be employed. These assays are described, among other places, in Maddox, et al. (supra). Such protocols provide a basis for diagnosing altered or abnormal levels of Kv-SL expression. Normal or standard values for Kv-SL expression are established by combining cell extracts taken from normal subjects, preferably human, with antibody to Kv-SL under conditions suitable for complex formation which are well known in the art. The amount of standard complex formation may be quantified by various methods, preferably by photometric methods. Then, standard values obtained from normal samples may be compared with values obtained from samples from subjects potentially affected by disease. Deviation between standard and subject values establishes the presence of disease state.

The antibody assays are useful to determine the level of Kv-SL present in a particular tissue, e.g., biopsied tumor tissue or neuronal tissue, as an indication of whether Kv-SL is being overexpressed or underexpressed in the tissue, or as an indication of how Kv-SL levels are responding to drug treatment.

B. Therapeutic Uses

In conditions associated with Kv-SL, including but not limited to those described in Section III.C above, therapeutic value may be achieved by administering an antibody specific against Kv-SL, to inhibit, for example, binding of an agonist to Kv-SL, or to block Kv-SL associated ion current.

The antibody employed is preferably a humanized monoclonal antibody, or a human Mab produced by known globulin-gene library methods. The antibody is administered typically as a sterile solution by IV injection, although other parenteral routes may be suitable. Typically, the antibody is administered in an amount between about 1–15 mg/kg body weight of the subject. Treatment is continued, e.g., with dosing every 1–7 days, until a therapeutic improvement is seen.

The following examples illustrate but in no way are intended to limit the present invention.

Materials

Unless otherwise indicated, restriction enzymes and DNA modifying enzymes were obtained from New England Biolabs (Beverly, Mass.) or Boehringer Mannheim (Indianapolis, Ind.). Nitrocellulose paper was obtained from Schleicher and Schuell (Keene, N. H.). Materials for SDS-polyacrylamide gel electrophoresis (SDS-PAGE) were obtained from Bio-Rad Laboratories (Hercules, Calif.). Other chemicals were purchased from Sigma (St. Louis, Mo.) or United States Biochemical (Cleveland, Ohio).

EXAMPLE 1

Identification of Mouse mKv-SL1 and mKv-SL2 DNA Sequences

A mouse brain plasmid cDNA library, obtained from Life Technologies(Gaithersburg, Md., Product #10655-017) was plated on thirty 15-cm dishes (10,000 colonies per dish). Bacterial colonies were lifted onto Hybond N filters (Amersham, Arlington Heights, Ill.) in duplicate.

Labeled EST7760 probe, based on a human EST sequence having similarity to the Shab potassium channel from Drosophila (GenBank Accession Number H85737), and having the sequence presented as SEQ ID NO:1, was synthesized using the REDI-PRIME kit (Amersham, Arlington Heights, Ill.) following instructions supplied with the kit. The filters were prehybridized without probe in Church's buffer (0.5 M phosphate buffer, pH 7.2; 1% bovine serum albumin; 7% SDS, 1 mM EDTA) at 50° C. for 2 hours, and then hybridized with probe overnight. The filters were then washed twice for 20 minutes each at room temperature in 2×SSC/0.1% SDS, and twice for 20 minutes each at 50° C. in 0.1×SSC/0.1% SDS. Signals were detected after 1–2 days of exposure of the filters to X-ray film.

Positive colonies were subjected to secondary and tertiary screenings. Positive colonies from tertiary screening were cultured and plasmid DNA was isolated using the QIAGEN miniprep kit (Qiagen, Santa Clarita, Calif.). The isolated DNAs were identified by DNA sequencing.

The above analysis resulted in the identification of partial DNA sequences of the mouse homolog of the human Kv-SL1 potassium channel. To obtain full-length clones, the GENE-TRAP cDNA Selection System from Life Technologies (Gaithersburg, Md.) was used according to the manufacturer's instructions. The DNA sequence encoding full-length mKv-SL1 is provided herein as SEQ ID NO:2. The translated amino acid sequence is provided as SEQ ID NO:3.

Similar library screening procedures were used for the identification of mouse Kv-SL2 clones, using a 400-bp EcoR1 fragment of a human Kv-SL2 partial clone (331C2) as a probe. The DNA sequence encoding full-length mKv-SL2 is provided herein as SEQ ID NO:6. The translated amino acid sequence is provided as SEQ ID NO:7.

EXAMPLE 2

Identification of Human hKv-SL1 and hKv-SL2 DNA Sequences

A XTRIPLEX human brain 5'-STRETCH PLUS cDNA library, obtained from Clontech Laboratories, Inc. (Palo Alto, Calif.; Product #HL5018t, Lot #5Y073) was plated on ten 15-cm dishes ($1.5\times10^5$ plaques per dish) containing an XL-1 BLUE bacterial lawn according to manufacturer's instructions (λTRIPLEX Library User Manual—products PT3003-1, PT1010-1, available, e.g., at URL http://www.clontech.com/). Plaques were lifted onto HYBOND PLUS filters (Amersham) in duplicate.

Labeled EST7760 probe based on the sequence presented as SEQ ID NO:1(above) was synthesized as above. The filters were prehybridized without probe in EXPRESSHYB (Clontech) for 0.5 hours at 68° C., and then hybridized with probe at $2\times10^6$ cpm/ml in EXPRESSHYB overnight at 68° C. The filters were then washed rapidly several times at room temperature in 2×SSC/0.05% SDS (40–60 min total), and twice for 20 min each at 50° C. in 0.1×SSC/0.1% SDS. Signal was detected after a three day exposure of the filters to X-ray film.

Positive plaques were subjected to secondary and tertiary screens. Phage from positive tertiary plaques were used to infect BM25.8 bacteria resulting in excision of plasmid DNA from the phage genomes. Plasmids isolated as described above were sequenced and/or subjected to dot-blot analyses using the probe sequence described above to identify potassium channel-encoding DNA sequences.

Dot blot analyses were performed as follows: bacteria containing plasmids which tested positive in the tertiary screen described above were grown in liquid LB broth overnight at 37° C. 150 μl of the liquid culture was then pelleted by low-speed centrifugation and the pellet was resuspended in 15 μl water. The suspension was boiled for 5 min, and 1.5 μl of boiled lysate dotted onto "HYBOND" Plus and probed with radiolabeled EST7760 probe as above. In certain experiments, the "boiling" step was replaced by the addition of 0.5 N NaOH for 5 min.

Clones which were labeled in the dot-blot were analyzed further, typically by polymerase chain reaction (PCR; Mullis, K. B., U.S. Pat. No. 4,683,202, issued Jul. 28, 1987; Mullis, K. B., et al., U.S. Pat. No. 4,683,195, issued Jul. 28, 1987) to determine the size of the inserts, and by sequencing of selected clones. The sequences were aligned and divided into groups, with each group representing the sequence of a potentially different potassium channel.

The above analyses resulted in the identification of DNA sequences of two novel human potassium channels, termed human Kv-SL1 (corresponding to above mouse Kv-SL1) and human Kv-SL2 (corresponding to above mouse Kv-SL2). The nucleic acid sequences are provided herein as SEQ ID NO:4 (hKv-SL1) and SEQ ID NO:8 (hKv-SL2). The translated amino acid sequences are given as SEQ ID NO:5 and SEQ ID NO:9, respectively.

To isolate cDNA molecules encoding full-length Kv-SL2, a modified procedure of Shepard & Rae (1997; Nucleic Acids Res. 25:3183–3185) was employed on cDNAs prepared from a plasmid cDNA library from Edge Biosystems (Gaithersburg, Md.). Briefly, 10 to 20 μg cDNA was mixed with 50–80 ng biotinylated oligonucleotide, 50 ng of each clamp oligo, and 1 μl of 1N NaOH in a total volume of 10 μl. All the oligonucleotide sequences were derived from the partial sequence of hKv-SL2. After the mixture was incubate at RT for 15–20 min, 40 μl of neutralization solution (0.12 M Tris, pH 7, 2×SSPE, 0.1% Tween 20) was added, and further incubated at 37° C.–42° C. Two to three hours later, to the above reaction mix, 20 μl (200 μg) magnetic beads (Dynabeads) was added, and the mixture was further incubated at the above temperature for 30 min.

To recover captured cDNA molecules, the supernatant was removed and the magnetic beads were washed 5 times with 0.5×SSPE, 0.1% Tween 20. The beads were then further washed with TE once or twice. Finally, the captured cDNA was eluted with 10 μl of 0.5×TE at 70° C. for 5 min. The eluted plasmid cDNA was then transform into *E. coli* cells and transformants were plated on one or more 15-cm dishes (a few thousand colonies per dish). Bacterial colonies were lifted onto HYBOND N filters (Amersham) in duplicate.

Labeled insert of mKv-SL2 was used as hybridization probe. The filters were prehybridized without probe in Church's buffer at 50° C. for a few hours, and then hybridized with probe overnight. The filters were then washed twice for 20 minutes each at room temperature in 2×SSPE/0.1% SDS, and once for 15 minutes at 50° C. in 0.2×SSPE/0.5% SDS. Signals were detected after a few hours of exposure of the filters to X-ray film.

Positive colonies were subjected to secondary and tertiary screenings. Positive colonies from tertiary screening were cultured and plasmid DNA was isolated using the QIAGEN miniprep kit. The isolated DNAs were identified by DNA sequencing. The above analysis resulted in the identification of DNA encoding full-length hKv-SL2. The DNA sequence is provided herein as SEQ ID No: 11 (hKv-SL2). The translated amino acid sequence is given as SEQ ID NO: 12.

EXAMPLE 3

Northern Analysis

A. hKv-SL1: Multiple Tissue Northern Blots were purchased from Clontech. The cDNA probe was prepared from the EST7760 sequence. All procedures were performed as suggested in the Clontech User Manual.

B. hKv-SL2: Multiple Tissue Northern Blots were purchased from Clontech. High Efficiency Hybridization System (HS-114F) was purchased from Molecular Research Center (Cincinnati, Ohio). Briefly, the blot was first soaked in prehybridization solution (1% SDS and 0.1 M NaCl) for 30 min at room temperature, and was then incubated with HS-114 plus 100 g/ml salmon sperm DNA in the absence of probe for a few hours at 50° C. The cDNA probe (made from a 960 base-pair fragment of hKv-SL2) was then added and the blot was allowed to hybridize at 50° C. overnight. The blot was then washed under the following conditions: 2×SSC/0.05% SDS, RT, twice; 0.1×SSPE/0.1% SDS, 50° C., twice. After wash, the blot was exposed to X-ray film.

EXAMPLE 4

Whole Cell Patch Clamp of Stably Transfected Cells

Potassium currents can be measured by the patch clamp method in the whole cell configuration (Hamill, et al., 1981). Electrode resistances ranging from 2–6 MΩ are appropriate. Recordings can be made with either an Axopatch 1C or Axopatch 200A amplifier (Axon Instruments, Foster City, Calif.) interfaced to PCLMP6 software (Axon Instruments) for data acquisition and analysis.

Potassium currents are recorded utilizing an external bath solution consisting of (in mM): 140 sodium chloride, 5 potassium chloride, 10 HEPES, 2 calcium chloride, 1 magnesium chloride, and 12 glucose, adjusted to pH 7.4 with sodium hydroxide and 305 mOsM. The internal pipette solution consists of (in mM): 15 sodium chloride, 125 potassium methanesulphonate, 10 HEPES, 11 EGTA, 1 calcium chloride, 2 magnesium chloride and 59 glucose, adjusted to pH 7.4 with potassium hydroxide and 295 mOsM. For test application, cells are placed in a flow through chamber (0.5–1 ml/min). Currents are elicited by changing the voltage from a holding potential of −90 mV to 0 mV, as a step pulse of 30 msec. duration every 15 sec. Data are sampled at 5 KHz and filtered at 1 KHz. Leak and capacitance currents are subtracted after measuring currents elicited by hyperpolarizing pulses.

EXAMPLE 5

Anticonvulsant Activity: DBA/2 Mouse Seizure Model

DBA/2 mice (18–21 days old; approx. 7–10 g) are obtained from Jackson Laboratories, Bar Harbor, Maine, and are housed for a minimum of three days to acclimate them to laboratory conditions. On the day of the test, mice are injected i.c.v. into the lateral ventricle with vehicle or test compound (total volume: 5 μl) according to standard methods (Jackson and Scheideler, 1996) 30 minutes prior to exposure to sound stimulus. After injection, the mice are individually housed in observation chambers and are observed over the following 30 min. for evidence of shaking behavior (persistent whole body shakes) or any other abnormal behaviors. The animals are exposed to a high intensity sound stimulus (100–110 dB sinusoidal tone at 14 Hz for 30 s). Mice are observed for the presence of clonic and tonic seizures with full hindlimb extension during the 30 s exposure to the sound.

While the invention has been described with reference to specific methods and embodiments, it is appreciated that various modifications and changes may be made without departing from the invention.

It is claimed:

1. An isolated and substantially purified Kv-SL1 protein having an amino acid sequence at least 85% identical to SEQ ID NO:3, wherein said protein is a voltage gated potassium ion channel subunit capable of effecting or modulating potassium ion conductance when associated with additional Kv subunits to form a channel which selectively conducts potassium ions therethrough.

2. The protein of claim 1, wherein said protein has a sequence at least 90% identical to SEQ ID NO:3.

3. A polypeptide consisting of a sequence selected from the group consisting of (a) the sequence between amino acids 223 and 481 of SEQ ID NO:3, and (b) the sequence SEQ ID NO:5.

4. The protein of claim 1, wherein said protein comprises the sequence SEQ ID NO:5.

5. A polypeptide consisting of a sequence selected from the group consisting of:

(a) the sequence between amino acids 373 and 401 of SEQ ID NO:3, and (b) the sequence between amino acids 149 and 177 of SEQ ID NO:5.

6. The protein of claim 1, wherein said protein has a sequence at least 95% identical to SEQ ID NO:3.

7. The protein of claim 1, wherein said protein has a sequence at least 97% identical to SEQ ID NO:3.

8. The protein of claim 1, wherein said protein comprises a sequence having at least 97% sequence identity to the sequence SEQ ID NO: 10.

9. The polypeptide of claim 5, consisting of the sequence between amino acids 373 and 401 of SEQ ID NO:3.

10. The protein of claim 1, consisting of the sequence SEQ ID NO:3.

* * * * *